(12) United States Patent
Iinuma et al.

(10) Patent No.: US 8,987,486 B2
(45) Date of Patent: Mar. 24, 2015

(54) TRANS-2-DECENOIC ACID DERIVATIVE AND PHARMACEUTICAL AGENT CONTAINING THE SAME

(75) Inventors: Munekazu Iinuma, Gifu (JP); Shoei Furukawa, Gifu (JP); Mitsuru Naiki, Kato (JP); Tomonori Matsumoto, Kato (JP); Hachiro Sugimoto, Kyoto (JP)

(73) Assignees: Nagoya Industrial Science Research Institute, Nagoya-shi (JP); Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/883,205

(22) PCT Filed: Nov. 1, 2011

(86) PCT No.: PCT/JP2011/075228
§ 371 (c)(1),
(2), (4) Date: May 2, 2013

(87) PCT Pub. No.: WO2012/060396
PCT Pub. Date: May 10, 2012

(65) Prior Publication Data
US 2013/0225837 A1    Aug. 29, 2013

(30) Foreign Application Priority Data
Nov. 2, 2010    (JP) .................................. 2010-246503

(51) Int. Cl.
| | | |
|---|---|---|
| C07C 57/02 | (2006.01) | |
| A61K 31/231 | (2006.01) | |
| C07C 327/30 | (2006.01) | |
| C07C 217/08 | (2006.01) | |
| C07C 219/20 | (2006.01) | |
| C07C 233/09 | (2006.01) | |
| C07C 233/38 | (2006.01) | |
| C07C 327/22 | (2006.01) | |
| C07C 69/533 | (2006.01) | |
| C07C 219/08 | (2006.01) | |
| C07C 323/12 | (2006.01) | |
| C07D 295/13 | (2006.01) | |

(52) U.S. Cl.
CPC ............. *C07C 327/30* (2013.01); *A61K 31/231* (2013.01); *C07C 57/02* (2013.01); *C07C 217/08* (2013.01); *C07C 219/20* (2013.01); *C07C 233/09* (2013.01); *C07C 233/38* (2013.01); *C07C 327/22* (2013.01); *C07C 2101/08* (2013.01); *C07C 69/533* (2013.01); *C07C 219/08* (2013.01); *C07C 323/12* (2013.01); *C07D 295/13* (2013.01); *C07C 2101/14* (2013.01)
USPC .......................................... 554/103; 514/549

(58) Field of Classification Search
CPC ............................... C07C 57/02; A61K 31/231

USPC .......................................... 554/103; 514/549
See application file for complete search history.

(56) References Cited

U.S. PATENT DOCUMENTS

| | | |
|---|---|---|
| 2003/0096802 A1 | 5/2003 | Ohuchida et al. |
| 2006/0069104 A1 | 3/2006 | Matsuda et al. |
| 2007/0043114 A1 | 2/2007 | Tateishi et al. |
| 2007/0202188 A1 | 8/2007 | Ley et al. |
| 2008/0269219 A1 | 10/2008 | Momose et al. |
| 2009/0124701 A1 | 5/2009 | Langer et al. |
| 2010/0116642 A1 | 5/2010 | Krull et al. |
| 2012/0264959 A1 | 10/2012 | Iinuma et al. |

FOREIGN PATENT DOCUMENTS

| | | |
|---|---|---|
| JP | A-07-316092 | 12/1995 |
| JP | A-2000-007568 | 1/2000 |
| JP | A-2002-080467 | 3/2002 |
| JP | A-2003-113085 | 4/2003 |
| JP | A-2003-261545 | 9/2003 |
| JP | A-2007-510634 | 4/2007 |
| JP | A-2007-217311 | 8/2007 |
| JP | A-2010-505893 | 2/2010 |
| WO | WO 03/084542 A1 | 10/2003 |
| WO | WO 2005/032535 A1 | 4/2005 |
| WO | WO 2009/038110 A1 | 3/2009 |

OTHER PUBLICATIONS

Crombie (CAPLUS Abstract of: Journal of the Chemical Society (1952) 2997-3008).*
Concellon et al., "Stereospecific Cyclopropanation of Highly Substituted C—C Double Bonds Promoted by CrCl$_2$. Stereoselective Synthesis of Cyclopropanecarboxamides and Cyclopropyl Ketones," Organic Letters, 2007, vol. 9, No. 16, pp. 2981-2984.

(Continued)

*Primary Examiner* — Robert Havlin
(74) *Attorney, Agent, or Firm* — Oliff PLC

(57) ABSTRACT

An object of the present invention is to provide a novel trans-2-decenoic acid derivative or a pharmaceutically acceptable salt thereof and to provide a pharmaceutical agent which contains said compound as an active ingredient and has a highly safe neurotrophic factor-like activity or an alleviating action for side effect induced by administration of anti-cancer agents. The trans-2-decenoic acid derivative or a pharmaceutically acceptable salt thereof which is the compound of the present invention is specifically represented by the formula (1):

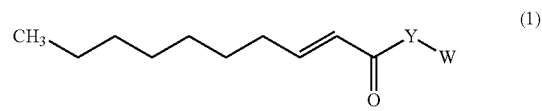

(In the formula, Y is —O—, —NR— or —S—, R is hydrogen atom, alkyl group, dialkylaminoalkyl group or the like and W is a substituent such as dialkylaminoalkyl group) and has a quite high usefulness as a pharmaceutical agent such as a preventive or therapeutic agent for dementia, Alzheimer's disease, Parkinson's disease, depression, etc., a treating or repairing agent for spinal cord injury.

23 Claims, 1 Drawing Sheet

(56) References Cited

OTHER PUBLICATIONS

Momose et al., "Association Studies of Multiple Candidate Genes for Parkinson's Disease using Single Nucleotide Polymorphisms," Annals of Neurology, 2002, vol. 51, No. 1, pp. 133-136.

Matsushita et al., "Brain-derived neurotrophic factor gene polymorphisms and Alzheimer's disease," Journal of Neural Transmission, 2005, vol. 112, pp. 703-711.

Sen et al., "A BDNF Coding Variant is Associated with the NEO Personality Inventory Domain Neuroticism, a Risk Factor for Depression," Neuropsychopharmacology, 2003, vol. 28, pp. 397-401.

Muller et al., "Brain-derived neurotrophic factor (BDNF) gene and rapid-cycling bipolar disorder," British Journal of Psychiatry, 2006, vol. 189, pp. 317-323.

Lang et al., "Association of a functional BDNF polymorphism and anxiety-related personality traits," Psychopharmacology, 2005, vol. 180, pp. 95-99.

Lynch et al., "Brain-Derived Neurotrophic Factor Restores Synaptic Plasticity in a Knock-In Mouse Model of Huntington's Disease," The Journal of Neuroscience, 2007, vol. 27, No. 16, pp. 4424-4434.

Duman et al., "A Role for MAP Kinase Signaling in Behavioral Models of Depression and Antidepressant Treatment," Biol. Psychiatry, 2007, vol. 61, pp. 661-670.

Ando, "Preparations of Z-$\alpha,\beta$-Unsaturated Amides by Using Horner-Wadsworth-Emmons Reagents, (Diphenylphosphono) acetamides," Synlett, 2001, No. 8, pp. 1272-1274.

Jan. 24, 2012 International Search Report issued in International Application No. PCT/JP2011/075228.

* cited by examiner

TRANS-2-DECENOIC ACID DERIVATIVE AND PHARMACEUTICAL AGENT CONTAINING THE SAME

TECHNICAL FIELD

The present invention relates to a novel trans-2-decenoic acid derivative or a pharmaceutically acceptable salt thereof and to a pharmaceutical agent containing said compound as an active ingredient. To be more specific, it relates to a trans-2-decenoic acid derivative or a pharmaceutically acceptable salt thereof having a neurotrophic factor-like activity such as nerve growth factor (NGF) or brain-derived neurotrophic factor (BDNF) or having an alleviating action for side effects induced by administration of anti-cancer agents and to a pharmaceutical agent containing said compound as an active ingredient.

BACKGROUND ART

Nerve cells are the cells having a signal transduction function and their injury is expressed as the severe loss of cranial nerve function. In the central nerves of brain and spinal cord, regeneration of axon is hardly expected and, when nerve cells are injured or denatured, it is necessary to protect and to activate the nerve cells. As the biophylaxis function as such, the role of neurotrophic factors in charge of differentiation of nerve cells, survival maintenance, promotion of synapse function and regeneration/repair of injured nerve axon is essential.

In the neurotrophic factors, nerve growth factor (NGF), brain-derived neurotrophic factor (BDNF), neurotrophin-3 (NT-3), neurotrophin-4/5 (NT-4/5), etc. constitute a neurotrophin family having not less than 50% of sequence homology where nerve growth factor (NGF) is a prototype. When neurotrophin secreted to outside of the cells is bound to high-affinity receptors (Trks) on nerve cell membranes, signals are transduced in three directions in the nerve cells. Via activation of MAP kinase signal transduction pathway including activation (phosphorylation) of MAP kinase (mitogen-activated protein (MAP) kinases/extracellular signal-regulated protein kinases 1/2 (ERK 1/2)) being one of the above, CREB (cAMP-response element binding protein) of transcription factor is activated whereupon many gene expressions are controlled. Accordingly, when the signal transduction via the MAP kinase signal transduction pathway is able to be activated, there is a possibility of its clinical application to nervous disorders caused by denaturation of nerve cells and cell death. There are also reports for the relation between the brain-derived neurotrophic factor (BDNF) and some diseases.

As a result of studies for genetic polymorphism of brain-derived neurotrophic factor (BDNF), there have been reports that the specific polymorphism relates to Parkinson's disease (refer to Non-Patent Document 1), to Alzheimer's disease (refer to Non-Patent Document 2), to depression (refer to Non-Patent Document 3), to bipolar depression (refer to Non-Patent Document 4) and to anxiety (refer to Non-Patent Document 5). There have been also reports that lowering of synapse function of gene-mutated mice of Huntington's disease is recovered by administration of the brain-derived neurotrophic factor (BDNF) (refer to Non-Patent Document 6) and that administration of an MAP kinase phosphorylation inhibitor induces the depressed state (refer to Non-Patent Document 7).

As will be noted from the examples of the above brain-derived neurotrophic factor (BDNF), neurotrophic factor shows a therapeutic effect to specific nerve diseases and has a sprouting and elongating action for axons. However, since neurotrophic factor is a high-molecular protein, there is a problem that, even when it is administered from periphery, it is unable to pass through a blood-brain barrier and hardly reaches the brain. Under such circumstances, there have been attempts for pharmaceutical agents which are low-molecular compounds and have neurotrophic factor-like activity activating the nerve cells and for pharmaceutical agents which promote the production and secretion of neurotrophic factor.

Until now, there have been proposals for the agents having a neurotrophic factor-like activity containing the compounds of predetermined general formulae (Patent Documents 1 and 2). There have been also proposals for the agents for accelerating the production/secretion of neurotrophic factor containing the compounds of predetermined general formulae (refer to Patent Documents 3 to 5) and for nerve regeneration promoters containing fatty acid compounds, salt thereof or prodrug thereof (refer to Patent Document 6).

There has been also a proposal for a medicament which contains the compound having a predetermined general formula and improves the lowering of response to GABA A receptor of astrocyte to prevent/treat the neurodegenerative disease, etc. (refer to Patent Document 7).

There has been also a proposal for an inducer of nerve cell differentiation where a medium-chain fatty acid having 6 to 10 carbons or methyl, ethyl, propyl or n-butyl ester of a medium-chain fatty acid having 6 to 10 chains is an active ingredient (refer to Patent Document 8).

There has been also mentioned that a fatty acid or a fatty acid ester has a neurotrophic factor-like activity (refer to Patent Document 9).

There has been also disclosed a fatty acid amide having tertiary amino group as a precursor of surface-active substances (refer to Patent Document 10).

PRIOR ART DOCUMENTS

Patent Documents

Patent Document 1: Japanese Patent Laid-Open No. 2000-7568
Patent Document 2: Japanese Patent Laid-Open No. 2003-113085
Patent Document 3: Japanese Patent Laid-Open No. 2002-80467
Patent Document 4: Japanese Patent Laid-Open No. 2003-261545
Patent Document 5: International Publication No. WO 2003/084542
Patent Document 6: International Publication No. WO 2005/032535
Patent Document 7: Japanese Patent Laid-Open No. Hei-07-316,092
Patent Document 8: Japanese Patent Laid-Open No. 2007-217,311
Patent Document 9: International Publication No. WO 2009-038110
Patent Document 10: Japanese Patent Laid-Open No. 2010-505893

Non-Patent Documents

Non-Patent Document 1: Ann. Neurol. 2002 January; 51(1) 133-6
Non-Patent Document 2: J. Neural Transm. 2005 May; 112 (5)703-11. Epub 2004 Sep. 14

Non-Patent Document 3: Neuropsychopharmacology. 2003 February; 28(2):397-401. Epub 2002 Aug. 29

Non-Patent Document 4: Br. J. Psychiatry. 2006 October; 189:317-23

Non-Patent Document 5: Psychopharmacology (Berl). 2005 June; 180(1):95-9. Epub 2005 Jan. 26

Non-Patent Document 6: J. Neurosci. 2007 Apr. 18; 27(16): 4424-34

Non-Patent Document 7: BIOL. PSYCHIATRY 2007; 61:661-670

SUMMARY OF THE INVENTION

Problems to be Solved by the Invention

However, in the agents having a neurotrophic factor-like activity or the production/secretion promoting agents for a neurotrophic factor mentioned in Patent Documents 1 to 5, neither fatty acid nor fatty acid derivative is an active ingredient. In the nerve regeneration promoter mentioned in Patent Document 6, the active ingredient for which pharmacological activity of nerve regeneration is disclosed is (2R)-2-propyloctanoic acid. In the medicament which prevents/treats the neurodegenerative disease, etc. mentioned in Patent Document 7, a saturated fatty acid having 10 carbons (C10) or less, an unsaturated fatty acid or a saturated fatty acid ester having 5 carbons (C5) or the like is an active ingredient. In the inducer of nerve cell differentiation mentioned in Patent Document 8, a medium-chain saturated fatty acid or an ester of the medium-chain saturated fatty acid having 6 to 10 carbons is an active ingredient. In Patent Document 9, a fatty acid or a fatty acid ester is an active ingredient. In Patent Document 10, there is no specific disclosure for a decenoic acid derivative and, further, there is no description for the neurotrophic factor-like activity.

An object of the present invention is to provide a novel trans-2-decenoic acid derivative or a pharmaceutically acceptable salt thereof and to provide a pharmaceutical agent which contains said compound as an active ingredient and has a highly safe neurotrophic factor-like activity or an alleviating action for side effect induced by administration of anti-cancer agents.

Means for Solving the Problems

As a result of intensive studies for solving the above problems by the present inventors, it has been found that a trans-2-decenoic acid derivative represented by the following formula (1) or a pharmaceutically acceptable salt has an excellent neurotrophic factor-like activity or an alleviating action (including the preventive and treating action in the present application; hereinafter, this term also has the same meaning) for side effect induced by administration of anti-cancer agents. As a result of further studies on the basis of such a finding, the present invention has now been accomplished.

Thus, the present invention provides the following compound (a decenoic acid derivative) and also provides a pharmaceutical agent (particularly, an agent having a neurotrophic factor-like activity and an agent for alleviating the side effect induced by administration of anti-cancer agents) containing said compound.

[1] A trans-2-decenoic acid derivative represented by the following formula (1') or a pharmaceutically acceptable salt thereof.

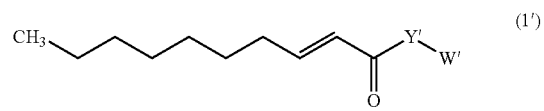

[In the formula,
Y' is —O—, —NR'— or —S—;
W' is W1' when Y' is —O—, W2' when Y' is —NR'— or W3' when Y' is —S—;
(1) W1' is dialkylaminoalkyl group, alkylthioalkyl group, alkoxyalkyl group, dialkoxyalkyl group or dialkylaminoalkoxyalkyl group;
(2-1) W2' is hydrogen atom, alkyl group or dialkylaminoalkyl group when R' is dialkylaminoalkyl group;
(2-2) W2' is alkyl group which is same as or different from R' when R' is alkyl group (except the case where both R' and W2' are ethyl group); or
(2-3) W2' is alkyl group (except 2-methylpropyl group and 2-methylbutyl group), cyclohexyl group or pyrrolidinealkyl group when R' is hydrogen atom; and
(3) W3' is alkyl group, cycloalkyl group, phenylalkyl group or dialkylaminoalkyl group]

[2] The trans-2-decenoic acid derivative or a pharmaceutically acceptable salt thereof according to [1], wherein Y' is —O— and W1' is dialkylaminoalkyl group, alkylthioalkyl group, alkoxyalkyl group, dialkoxyalkyl group or dialkylaminoalkoxyalkyl group.

[3] The trans-2-decenoic acid derivative or a pharmaceutically acceptable salt thereof according to [1], wherein Y' is —NR'—.

[4] The trans-2-decenoic acid derivative or a pharmaceutically acceptable salt thereof according to [3], wherein R' is dialkylaminoalkyl group and W2' is hydrogen atom, alkyl group or dialkylaminoalkyl group.

[5] The trans-2-decenoic acid derivative or a pharmaceutically acceptable salt thereof according to claim [3], wherein R' is alkyl group and W2' is alkyl group which is same as or different from R' (except the case where both R' and W2' are ethyl group).

[6] The trans-2-decenoic acid derivative or a pharmaceutically acceptable salt thereof according to [3], wherein R' is hydrogen atom and W2' is alkyl group (except 2-methylpropyl group and 2-methylbutyl group), cyclohexyl group or pyrrolidinealkyl group.

[7] The trans-2-decenoic acid derivative or a pharmaceutically acceptable salt thereof according to [1], wherein Y' is —S— and W3' is alkyl group, cycloalkyl group, phenylalkyl group or dialkylaminoalkyl group.

[8] A pharmaceutical agent containing a trans-2-decenoic acid represented by the following formula (1) or a pharmaceutically acceptable salt thereof as an active ingredient.

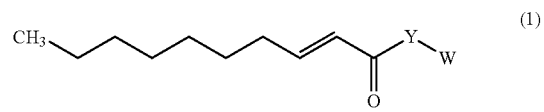

[In the formula,
Y is —O—, —NR— or —S—;
W is W1 when Y is —O—, W2 when Y is —NR— or W3 when Y is —S—;
(1) W1 is dialkylaminoalkyl group, alkylthioalkyl group, alkoxyalkyl group, dialkoxyalkyl group or dialkylaminoalkoxyalkyl group;

(2-1) W2 is hydrogen atom, alkyl group or dialkylaminoalkyl group when R is dialkylaminoalkyl group;

(2-2) W2 is alkyl group which is same as or different from R when R is alkyl group; or (2-3) W2 is alkyl group, cycloalkyl group, pyrrolidinealkyl group, phenyl group or phenylalkyl group when R is hydrogen atom; and (3) W3 is alkyl group, cycloalkyl group, phenylalkyl group or dialkylaminoalkyl group.]

[9] The pharmaceutical agent according to [8], wherein Y is —O— and W1 is dialkylaminoalkyl group, alkylthioalkyl group, alkoxyalkyl group, dialkoxyalkyl group or dialkylaminoalkoxyalkyl group.

[10] The pharmaceutical agent according to [8], wherein Y is —NR—.

[11] The pharmaceutical agent according to [10], wherein R is dialkylaminoalkyl group and W2 is hydrogen atom, alkyl group or dialkylaminoalkyl group.

[12] The pharmaceutical agent according to [10], wherein R is alkyl group and W2 is alkyl group which is same as or different from R.

[13] The pharmaceutical agent according to [11], wherein R is hydrogen atom and W2 is alkyl group, cycloalkyl group, pyrrolidinealkyl group, phenyl group or phenylalkyl group.

[14] The pharmaceutical agent according to [8], wherein Y is —S— and W3 is alkyl group, cycloalkyl group, phenylalkyl group or dialkylaminoalkyl group.

[15] The pharmaceutical agent according to any of [8] to [14], wherein the pharmaceutical agent is an agent having a neurotrophic factor-like activity.

[16] The pharmaceutical agent according to any of [8] to [14], wherein the pharmaceutical agent is a preventive or therapeutic agent for a nervous disorder.

[17] The pharmaceutical agent according to [16], wherein the nervous disorder is a neurodegenerative disease.

[18] The pharmaceutical agent according to [17], wherein the neurodegenerative disease is dementia, Alzheimer's disease, Parkinson's disease, amyotrophic lateral sclerosis (ALS), Huntington's disease, progressive supranuclear palsy (PSP) or diabetic neuropathy.

[19] The pharmaceutical agent according to [16], wherein the nervous disorder is a mental disease.

[20] The pharmaceutical agent according to [19], wherein the mental disease is depression.

[21] The pharmaceutical agent according to [19], wherein the mental disease is anxiety disorder (neurosis).

[22] The pharmaceutical agent according to any of [8] to [14], wherein the pharmaceutical agent is a treating agent or a repairing agent for spinal cord injury.

[23] The pharmaceutical agent according to any of claims [8] to [14], wherein the pharmaceutical agent is an alleviating agent for side effect induced by administration of anti-cancer agents.

[24] The pharmaceutical agent according to [23], wherein the side effect induced by administration of anti-cancer agents is a peripheral nerve disorder.

[25] The compound or a pharmaceutically acceptable salt thereof according to any of [8] to [14], which is used for treating the disease according to any of [16] to [22].

[26] The compound or a pharmaceutically acceptable salt thereof according to any of [8] to [14], which is used for treating the side effect (particularly, a peripheral nerve disorder) induced by administration of anti-cancer agents.

[27] A method for treating the disease according to any of [16] to [22], wherein the compound or a pharmaceutically acceptable salt thereof according to any of [8] to [14] in an active dose is administered to a patient suffering from the disease according to any of [16] to [22].

[28] A method for treating the side effect induced by administration of anti-cancer agents, wherein the compound or a pharmaceutically acceptable salt thereof according to any of [8] to [14] in an active dose is administered to a patient suffering from the side effect (particularly, a peripheral nerve disorder) induced by administration of anti-cancer agents.

[29] Use of the compound or a pharmaceutically acceptable salt thereof according to any of [8] to [14] in the manufacture of the pharmaceutical agent for treating the disease according to any of [16] to [22].

[30] Use of the compound or a pharmaceutically acceptable salt thereof according to any of [8] to [14] in the manufacture of the pharmaceutical agent for treating the side effect (particularly, a peripheral nerve disorder) induced by administration of anti-cancer agents.

Advantages of the Invention

Since the compound of the present invention has an excellent neurotrophic factor-like activity, it is used as an agent having a neurotrophic factor-like activity. Due to the neurotrophic factor-like activity, this agent having a neurotrophic factor-like activity activates the signal transduction via an MAP kinase signal transduction pathway and is useful as a highly safe preventive or therapeutic agent for a nervous disorder.

Among the nervous disorders, this agent is particularly useful as a preventive or treating agent (improving agent) for a neurodegenerative disease such as dementia, Alzheimer's disease, Parkinson's disease, amyotrophic lateral sclerosis (ALS), Huntington's disease, progressive supranuclear palsy (PSP), diabetic neuropathy or glaucoma which is an optic nerve disease.

Further, this agent is particularly useful as a preventive/improving agent for a mental disease in the nervous disorder. Among the mental diseases, this agent is particularly useful as a preventive or improving agent for depression and anxiety disorder (neurosis) and particularly achieves a fast-acting antidepressant and anti-anxiety effect as a preventive or treating agent (improving agent) for depression and anxiety disorder (neurosis).

Furthermore, the agent having a neurotrophic factor-like activity of the present invention is useful as a treating agent (repairing agent) for spinal cord injury and is able to be used for the repair of spinal injury particularly by means of administration into the body.

Still further, the compound of the present invention has an excellent pharmacological action which alleviates the side effect induced by administration of anti-cancer agents. It is particularly useful as an alleviating agent for a peripheral nerve disorder in the side effect accompanied by administration of anti-cancer agents.

MODE FOR CARRYING OUT THE INVENTION

Figure 1:
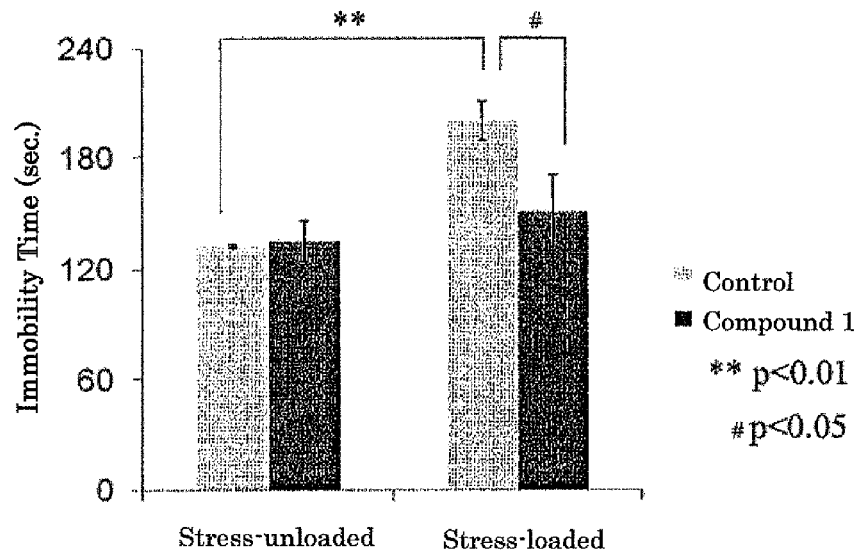
FIG. 1 is a graph showing the immobility time of mice in the stress-loaded and stress-unloaded examples in the control and the administration of the compound 1 on the thirteenth day after loaded with the stress by forced swimming in Test Example 3.

The present invention provides a trans-2-decenoic acid derivative represented by the following formula (1') or a pharmaceutically acceptable salt thereof.

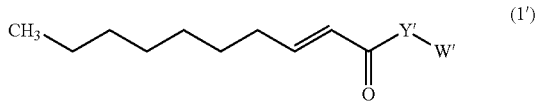

(1')

[In the formula,
Y' is —O—, —NR'— or —S—;
W' is W1' when Y' is —O—, W2' when Y' is —NR'— or W3' when Y' is —S—;
(1) W1' is dialkylaminoalkyl group, alkylthioalkyl group, alkoxyalkyl group, dialkoxyalkyl group or dialkylaminoalkoxyalkyl group;
(2-1) W2' is hydrogen atom, alkyl group or dialkylaminoalkyl group when R' is dialkylaminoalkyl group;
(2-2) W2' is alkyl group which is same as or different from R' when R' is alkyl group (except the case where both R' and W2' are ethyl group); or
(2-3) W2' is alkyl group (except 2-methylpropyl group and 2-methylbutyl group), cyclohexyl group or pyrrolidinealkyl group when R' is hydrogen atom; and
(3) W3' is alkyl group, cycloalkyl group, phenylalkyl group or dialkylaminoalkyl group.]

The "alkyl" in "aminoalkyl" when W1' is "dialkylaminoalkyl group" in the substituent of the above formula (1') is preferably a linear or branched alkyl group having 1 to 10 carbon(s) such as methyl, ethyl, propyl, isopropyl, butyl, isobutyl, sec-butyl, tert-butyl, pentyl, isopentyl, neopentyl, tert-pentyl, dimethylpropyl, hexyl, isohexyl, heptyl, isoheptyl, octyl, isooctyl, nonyl, isononyl, decyl or isodecyl and, more preferably, a linear or branched alkyl group having 1 to 6 carbon(s).

Each of the "alkyl" when both R' and W2' are alkyl group is same or different and is preferably a liner or branched alkyl group having 1 to 10 carbon(s) such as methyl, ethyl, propyl, isopropyl, butyl, isobutyl, sec-butyl, tert-butyl, pentyl, isopentyl, neopentyl, tert-pentyl, hexyl, isohexyl, heptyl, isoheptyl, octyl, isooctyl, nonyl, isononyl, decyl or isodecyl and, more preferably, a liner or branched alkyl group having 1 to 7 carbon(s). However, the case where both R' and W2' are ethyl is excluded.

The "alkyl" when R' is hydrogen atom and W2' is alkyl group is preferably a liner or branched alkyl group having 1 to 10 carbon(s) such as methyl, ethyl, propyl, isopropyl, butyl, isobutyl, sec-butyl, tert-butyl, pentyl, isopentyl, neopentyl, tert-pentyl, hexyl, isohexyl, heptyl, isoheptyl, 1-propylbutyl, octyl, isooctyl, 1-ethylhexyl, 1,1,3,3-tetramethylbutyl, nonyl, isononyl, decyl or isodecyl and, more preferably, a liner or branched alkyl group having 1 to 8 carbon(s). However, the case where it is 2-methylpropyl group or 2-methylbutyl group is excluded.

The "alkyl" when W3' is alkyl group is preferably a liner or branched alkyl group having 1 to 12 carbon(s) such as methyl, ethyl, propyl, isopropyl, butyl, isobutyl, sec-butyl, tert-butyl, pentyl, isopentyl, neopentyl, tert-pentyl, hexyl, isohexyl, heptyl, isoheptyl, octyl, isooctyl, nonyl, isononyl, decyl, isodecyl, undecyl, isoundecyl, dodeyl or isododecyl and, more preferably, a liner or branched alkyl group having 4 to 10 carbons.

The "cycloalkyl group" is preferably a cycloalkyl group having 3 to 8 carbons such as cyclopropyl, cyclobutyl, cyclopentyl, cyclohexyl, cycloheptyl or cyclooctyl and, more preferably, a cycloalkyl group having 5 or 6 carbons.

The "alkyl" which is other than the above-specified ones is preferably a liner or branched alkyl group having 1 to 4 carbon(s) such as methyl, ethyl, propyl, isopropyl, butyl, isobutyl, sec-butyl or tert-butyl.

The "alkoxy" in the substituent of the above formula (1') is preferably a liner or branched alkoxy group having 1 to 4 carbon(s) such as methoxy, ethoxy, propoxy, isopropoxy, butoxy, isobutoxy, sec-butoxy or tert-butoxy.

Preferred examples of the compound represented by the above formula (1') include those where Y' is —O— and W1' is dialkylaminoalkyl group.

Other preferred examples include those where Y' is —O— and W1' is alkylthioalkyl group.

Other preferred examples include those where Y' is —O— and W1' is alkoxyalkyl group.

Other preferred examples include those where Y' is —O— and W1' is dialkoxyalkyl group.

Other preferred examples include those where Y' is —O— and W1' is dialkylaminoalkoxyalkyl group.

Other preferred examples include those where Y' is —NR'—, R' is dialkylaminoalkyl group and W2' is hydrogen atom.

Other preferred examples include those where Y' is —NR'—, R' is dialkylaminoalkyl group and W2' is alkyl group.

Other preferred examples include those where Y' is —NR'—, R' is dialkylaminoalkyl group and W2' is dialkylaminoalkyl group.

Other preferred examples include those where Y' is —NR'—, R' is alkyl group and W2' is alkyl group which is same as or different from if (except the case where both R' and W2' are ethyl group).

Other preferred examples include those where Y' is —NR'—, R' is hydrogen atom and W2' is alkyl group (except 2-methylpropyl group and 2-methylbutyl group).

Other preferred examples include those where Y' is —NR'—, R' is hydrogen atom and W2' is cyclohexyl group.

Other preferred examples include those where Y' is —NR'—, R' is hydrogen atom and W2' is pyrrolidinealkyl group.

Other preferred examples include those where Y' is —S— and W3' is alkyl group.

Other preferred examples include those where Y' is —S— and W3' is cycloalkyl group.

Other preferred examples include those where Y' is —S— and W3' is phenylalkyl group.

Other preferred examples include those where Y' is —S— and W3' is dialkylaminoalkyl group.

The present invention also relates to a pharmaceutical agent such as an agent having a neurotrophic factor-like activity or an agent for alleviating the side effect induced by administration of anti-cancer agents where the pharmaceutical agent contains at least one member of a trans-2-decenoic acid derivative represented by the following formula (1) and a pharmaceutically acceptable salt thereof as an active ingredient. The compound represented by the formula (1) covers the compound represented by the above-mentioned formula (1').

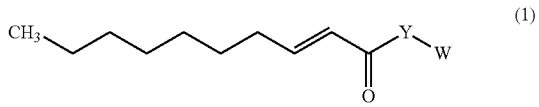

(1)

[In the formula,

Y is —O—, —NR— or —S—;

W is W1 when Y is —O—, W2 when Y is —NR— or W3 when Y is —S—;

(1) W1 is dialkylaminoalkyl group, alkylthioalkyl group, alkoxyalkyl group, dialkoxyalkyl group or dialkylaminoalkoxyalkyl group;

(2-1) W2 is hydrogen atom, alkyl group or dialkylaminoalkyl group when R is dialkylaminoalkyl group;

(2-2) W2 is alkyl group which is same as or different from R when R is alkyl group;

(2-3) W2 is alkyl group, cycloalkyl group, pyrrolidinealkyl group, phenyl group or phenylalkyl group when R is hydrogen atom; and (3) W3 is alkyl group, cycloalkyl group, phenylalkyl group or dialkylaminoalkyl group.]

The "alkyl" in the "aminoalkyl" when W1 is "dialkylaminoalkyl group" in the substituent of the above formula (1) is the same as the "alkyl" in the "aminoalkyl" when W1' is "dialkylaminoalkyl group" in the substituent of the above formula (1').

Each of the "alkyl" when both R and W2 are alkyl group which is same or different and is preferably a liner or branched alkyl group having 1 to 10 carbon(s) such as methyl, ethyl, propyl, isopropyl, butyl, isobutyl, sec-butyl, tert-butyl, pentyl, isopentyl, neopentyl, tert-pentyl, hexyl, isohexyl, heptyl, isoheptyl, octyl, isooctyl, nonyl, isononyl, decyl or isodecyl and, more preferably, a liner or branched alkyl group having 1 to 7 carbon(s).

The "alkyl" when R is hydrogen atom and W2 is alkyl group is preferably a liner or branched alkyl group having 1 to 10 carbon(s) such as methyl, ethyl, propyl, isopropyl, butyl, isobutyl, sec-butyl, tert-butyl, pentyl, isopentyl, neopentyl, tert-pentyl, hexyl, isohexyl, heptyl, isopentyl, 1-propylbutyl, octyl, isooctyl, 1-ethylhexyl, 1,1,3,3-tetramethylbutyl, nonyl, isononyl, decyl or isodecyl and, more preferably, a liner or branched alkyl group having 1 to 8 carbon(s).

The "alkyl" when W3 is alkyl group is the same as the "alkyl" when W3' in the substituent of the above formula (1') is alkyl group.

The "cycloalkyl group" is the same as the "cycloalkyl group" in the substituent of the above formula (1').

The "alkyl" in the substituent of the above formula (1) which is other than the above-specified ones is preferably a liner or branched alkyl group having 1 to 4 carbon(s) such as methyl, ethyl, propyl, isopropyl, butyl, isobutyl, sec-butyl or tert-butyl.

The "alkoxy" in the substituent of the above formula (1) is the same as the "alkoxy" in the substituent of the above formula (1').

Preferred examples of the compound represented by the above formula (1) include those where Y is —O— and W1 is dialkylaminoalkyl group.

Other preferred examples include those where Y is —O— and W1 is alkylthioalkyl group.

Other preferred examples include those where Y is —O— and W1 is alkoxyalkyl group.

Other preferred examples include those where Y is —O— and W1 is dialkoxyalkyl group.

Other preferred examples include those where Y is —O— and W1 is dialkyaminoalkoxyalkyl group.

Other preferred examples include those where Y is R is dialkylaminoalkyl group and W2 is hydrogen atom.

Other preferred examples include those where Y is —NR—, R is dialkylaminoalkyl group and W2 is alkyl group.

Other preferred examples include those where Y is —NR—, R is dialkylaminoalkyl group and W2 is dialkylaminoalkyl group.

Other preferred examples include those where Y is R is alkyl group and W2 is alkyl group which is same as or different from R.

Other preferred examples include those where Y is —NR—, R is hydrogen atom and W2 is alkyl group.

Other preferred examples include those where Y is —NR—, R is hydrogen atom and W2 is cycloalkyl group.

Other preferred examples include those where Y is R is hydrogen atom and W2 is pyrrolidinealkyl group.

Other preferred examples include those where Y is —NR—, R is hydrogen atom and W2 is phenyl group.

Other preferred examples include those where Y is —NR—, R is hydrogen atom and W2 is phenylalkyl group.

Other preferred examples include those where Y is —S— and W3 is alkyl group.

Other preferred examples include those where Y is —S— and W3 is cycloalkyl group.

Other preferred examples include those where Y is —S— and W3 is phenylalkyl group.

Other preferred examples include those where Y is —S— and W3 is dialkylaminoalkyl group.

Preferred compounds of the present invention are shown in Tables 1 to 4.

TABLE 1

| Compound No. | Compound Name | Structural Formula |
|---|---|---|
| 1 | (E)-2-(dimethylamino)ethyl dec-2-enoate | |
| 2 | (E)-3-(dimethylamino)propyl dec-2-enoate | |

TABLE 1-continued

| Compound No. | Compound Name | Structural Formula |
|---|---|---|
| 3 | (E)-1-(dimethylamino)propan-2-yl dec-2-enoate | |
| 4 | (E)-4-(dimethylamino)butyl dec-2-enoate | |
| 5 | (E)-3-(dimethylamino)-2,2-dimethylpropyl dec-2-enoate | |
| 6 | (E)-2-(diethylamino)ethyl dec-2-enoate | |
| 7 | (E)-6-(dimethylamino)hexyl dec-2-enoate | |
| 8 | (E)-2-(isopropylthio)ethyl dec-2-enoate | |
| 9 | (E)-2-methoxyethyl dec-2-enoate | |
| 10 | (E)-2-ethoxyethyl dec-2-enoate | |
| 11 | (E)-1,3-diethoxy-2-propyl dec-2-enoate | |
| 12 | (E)-2-(2-(dimethylamino)ethoxy)ethyl dec-2-enoate | |
| 13 | (E)-2-(2-(diethylamino)ethoxy)ethyl dec-2-enoate | |
| 14 | (E)-3-(2-(diethylamino)ethoxy)propyl dec-2-enoate | |
| 15 | (E)-N-methyl dec-2-enamide | |

TABLE 1-continued

| Compound No. | Compound Name | Structural Formula |
|---|---|---|
| 16 | (E)-N-ethyl dec-2-enamide | 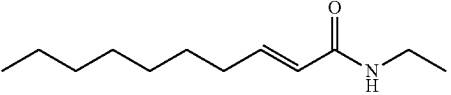 |
| 17 | (E)-N-butyl dec-2-enamide | 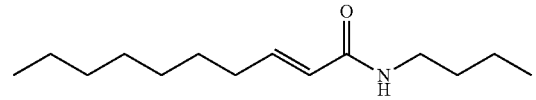 [SMILES: CCCCCCC/C=C/C(=O)NCCCC] |

TABLE 2

| Compound No. | Compound Name | Structural Formula |
|---|---|---|
| 18 | (E)-N-isobutyl dec-2-enamide | 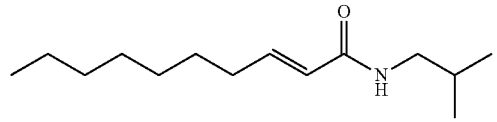 [SMILES: CCCCCCC/C=C/C(=O)NCC(C)C] |
| 19 | (E)-N-pentyl dec-2-enamide | 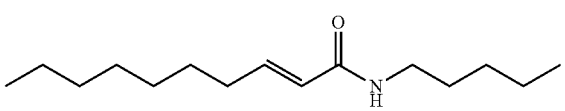 [SMILES: CCCCCCC/C=C/C(=O)NCCCCC] |
| 20 | (E)-N-isopentyl dec-2-enamide | 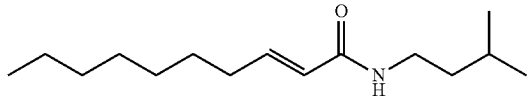 |
| 21 | (E)-N-tert-pentyl dec-2-enamide | 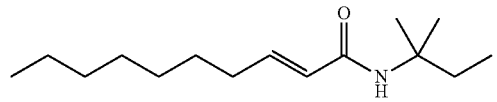 [SMILES: CCCCCCC/C=C/C(=O)NC(C)(C)CC] |
| 22 | (E)-N-hexyl dec-2-enamide | 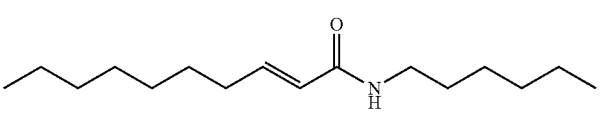 [SMILES: CCCCCCC/C=C/C(=O)NCCCCCC] |
| 23 | (E)-N-heptyl dec-2-enamide | 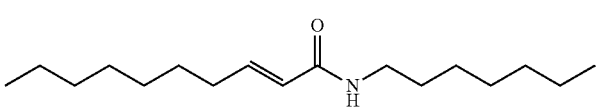 [SMILES: CCCCCCC/C=C/C(=O)NCCCCCCC] |
| 24 | (E)-N-(heptan-4-yl) dec-2-enamide | 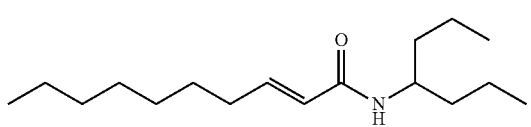 [SMILES: CCCCCCC/C=C/C(=O)NC(CCC)CCC] |
| 25 | (E)-N-(octan-3-yl) dec-2-enamide | 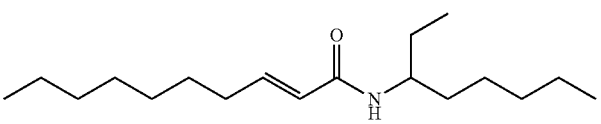 [SMILES: CCCCCCC/C=C/C(=O)NC(CC)CCCCC] |
| 26 | (E)-N-(2,4,4-trimethylpentan-2-yl) dec-2-enamide | 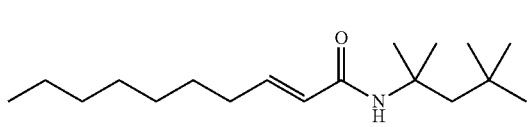 [SMILES: CCCCCCC/C=C/C(=O)NC(C)(C)CC(C)(C)C] |

TABLE 2-continued

| Compound No. | Compound Name | Structural Formula |
|---|---|---|
| 27 | (E)-N-cyclohexyl dec-2-enamide | |
| 28 | (E)-N-phenyl dec-2-enamide | |
| 29 | (E)-N-phenethyl dec-2-enamide | |
| 30 | (E)-N-(2-pyrrolidin-1-ylethyl) dec-2-enamide | |
| 31 | (E)-N,N-diethyl dec-2-enamide | |
| 32 | (E)-N,N-dibutyl dec-2-enamide | |
| 33 | (E)-N,N-dipentyl dec-2-enamide | |

TABLE 3

| Compound No. | Compound Name | Structural Formula |
|---|---|---|
| 34 | (E)-N,N-dihexyl dec-2-enamide | |
| 35 | (E)-N-ethyl-N-heptyl dec-2-enamide | |
| 36 | (E)-N-2-(dimethylamino)ethyl dec-2-enamide | |

TABLE 3-continued

| Compound No. | Compound Name | Structural Formula |
|---|---|---|
| 37 | (E)-N-2-(diethylamino)ethyl dec-2-enamide | |
| 38 | (E)-N-3-(dimethylamino)propyl dec-2-enamide | |
| 39 | (E)-N-3-(diethylamino)propyl dec-2-enamide | |
| 40 | (E)-N-2-(diisopropylamino)ethyl dec-2-enamide | |
| 41 | (E)-N-2-(dibutylamino)ethyl dec-2-enamide | |
| 42 | (E)-N-(2-(dimethylamino)ethyl)-N-methyl dec-2-enamide | |
| 43 | (E)-N-(2-(dimethylamino)ethyl)-N-ethyl dec-2-enamide | |
| 44 | (E)-N-(2-(diethylamino)ethyl)-N-ethyl dec-2-enamide | |
| 45 | (E)-N,N-bis(2-(dimethylamino)ethyl) dec-2-enamide | |

TABLE 4

| Compound No. | Compound Name | Structural Formula |
|---|---|---|
| 46 | (E)-N,N-bis(2-(diethylamino)ethyl) dec-2-enamide | |
| 47 | (E)-N,N-bis(3-(dimethylamino)propyl) dec-2-enamide | |
| 48 | (E)-S-pentyl dec-2-enethioate | |
| 49 | (E)-S-isopentyl dec-2-enethioate | |
| 50 | (E)-S-hexyl dec-2-enethioate | |
| 51 | (E)-S-heptyl dec-2-enethioate | |
| 52 | (E)-S-decyl dec-2-enethioate | |
| 53 | (E)-S-cyclopentyl dec-2-enethioate | |
| 54 | (E)-S-phenethyl dec-2-enethioate | |
| 55 | (E)-S-2-(dimethylamino)ethyl dec-2-enethioate | |
| 56 | (E)-S-2-(diethylamino)ethyl dec-2-enethioate | |

The compound of the present invention represented by the formula (1) (including the compound represented by the formula (1') as well; it is also the same in the following description) is able to be produced using trans-2-decenoic acid as a material. The compound represented by the formula (1) is able to be produced, for example, as shown in the following reaction formulae.

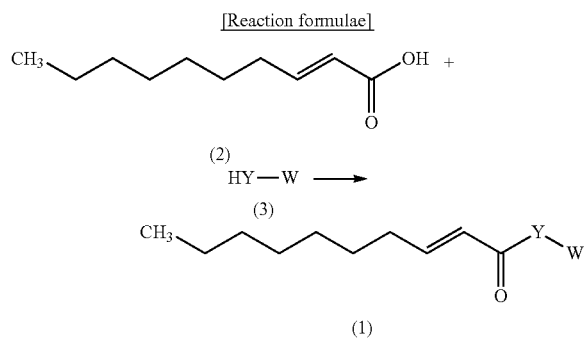

[Reaction formulae]

(In the formulae, Y and W are the same as those mentioned already.)

The compound represented by the formula (1) is able to be produced by subjecting the compound represented by the formula (2) and the compound represented by the formula (3) to a dehydration-condensation. The dehydration-condensation reaction may adopt the conventionally known methods.

For example, the compound represented by the formula (2) may be made to react with the compound represented by the formula (3) in the presence of an appropriate condensing agent (such as dicyclohexylcarbodiimide (DCC) or N-(3-dimethylaminopropyl)-N'-ethylcarbodiimide.HCl). The reaction may be usually carried out in a common solvent (such as dichloromethane). Usually, the using amount of the compound represented by the formula (3) is 0.5 to 2 mol (preferably, 1 to 1.5 mol) to 1 mol of the compound represented by the formula (2).

Alternatively, the compound represented by the formula (2) may be, for example, once converted to a carboxylic halide and then made to react with the compound represented by the formula (3) in the presence or absence of a base. Conversion to the carboxylic halide may be carried out, for example, using a halogenating agent such as thionyl chloride, sulfyryl chloride, phosphorus trichloride, phosphorus pentachloride, oxalyl chloride or phosphoric acid trichloride. Examples of the base include triethylamine and pyridine. Usually, the using amount of the compound represented by the formula (3) is 0.5 to 2 mol (preferably, 1 to 1.5 mol) to 1 mol of the compound represented by the formula (2). When a base is used, the using amount of the base is usually about 1 to 5 mol to 1 mol of the compound represented by the formula (2).

After finishing the above reaction, the aimed compound is able to be produced using the known purifying and isolating operations (such as extraction, chromatography, distillation or recrystallization).

The compound of the present invention represented by the formula (1) includes not only and naturally the above-mentioned free form but also the forms of salt, solvate and prodrug. In forming the salt, the form of a pharmaceutically acceptable salt is advantageous in using as a pharmaceutical agent. Examples of the salt include that with an inorganic acid such as phosphoric acid, hydrochloric acid, sulfuric acid or nitric acid and that with an organic acid such as citric acid, tartaric acid, lactic acid or glycolic acid.

Examples of the solvate include hydrate and a solvate with alcohol.

When the compound of the present invention represented by the formula (1) contains asymmetric carbon(s), it includes various kinds of isomers such as optical isomer, racemic substance or diastereomer. When the compound of the present invention becomes crystals, it also includes various kinds of crystal forms (crystal polymorphism) being able to be formed thereby.

Since the compound of the present invention represented by the formula (1) has a neurotrophic factor-like activity, it is useful as an agent having a neurotrophic factor-like activity. The agent having a neurotrophic factor-like activity according to the present invention is useful for the prevention or the treatment of a nervous disorder. The term nervous disorder means a morbid state where function of nerve cells is deteriorated caused by nerve cell degeneration or cell death and includes a neurodegenerative disease and a mental disease. The neurodegenerative disease stands for dementia, Alzheimer's disease, Parkinson's disease, amyotrophic lateral sclerosis (ALS), Huntington's disease, progressive supranuclear palsy (PSP), diabetic neuropathy or glaucoma which is an optic nerve disease. The mental disease stands for depression (including bipolar depression), anxiety disorder (neurosis), schizophrenia, etc. In using for depression, the conventional treating agent for depression such as tricyclic antidepressant, tetracyclic antidepressant, selective serotonin reuptake inhibitor (SSRI) or serotonin-noradrenaline reuptake inhibitor (SNRI) needs at least three to four weeks until the effect appears and, during that period, the agent is to be periodically administered. However, the agent having a neurotrophic factor-like activity according to the present invention is able to be expected to have more instant effect than the conventional ones.

The agent having a neurotrophic factor-like activity according to the present invention is useful as a treating agent or a repairing agent for spinal cord injury. There has been no effective treating method for the spinal cord injury where spinal cord suffers from physical injury due to traffic accident, sport accident, compression fracture of elderly persons, etc. and various treating methods by means of regenerative therapy have been investigated. According to the agent having a neurotrophic factor-like activity of the present invention, a highly safe unsaturated fatty acid ester is an active ingredient and it is expected that the spinal cord injury is able to be treated or repaired by administration into the body.

Further, the compound of the present invention represented by the formula (1) has a prophylactic or alleviating action for the side effects induced by administration of anti-cancer agents and is particularly effective as an alleviating agent for a peripheral nerve disorder. The anti-cancer agent developing the peripheral nerve disorder in the present invention is an anti-cancer agent that specifically damages microtubules to induce the peripheral nerve disorder. Examples of such medicinal agent include taxane drugs such as paclitaxel or docetaxel and a vinca alkaloid drugs such as vincristine, vinblastine, vindesine or vinorelbine. In addition, examples of the medicinal agent that damages nerve cells to cause axonopathy and then induces the peripheral nerve disorder include platinum drugs such as oxaliplatin, carboplatin, cisplatin or nedaplatin.

Examples of the peripheral nerve disorder induced by these anti-cancer agents include pain such as a stinging pain and burning pain, paresthesia such as numbness of limb extremities and a burning sensation, hyperesthesia such as hypersensitivity to cold stimuli, dysesthesia such as sensory loss, sensory paralysis and sense of discomfort, sensory ataxia and muscle weakness. The peripheral nerve disorder induced by an anti-cancer agent that the compound of the present invention is intended to improve includes a peripheral nerve disorder induced by monotherapy using one type of anti-cancer agent as well as a peripheral nerve disorder induced by multiple drug therapy in which a plurality of medicinal agents having various action mechanisms is administered or by biochemical modulation in which a combination of medicinal agents and an administration method are designed such that the medicinal agents having various action mechanisms can provide the maximum effectiveness.

There is no particular limitation for the dosage form as the pharmaceutical agents in the present invention and any of dosage forms for oral and parenteral routes may be acceptable. Further, an appropriate dosage form may be used depending upon the administering form and, for example, the pharmaceutical agents may be prepared into various kinds of pharmaceutical preparations including injection preparation, oral preparation such as capsules, tablets, granules, powders, pills or fine granules, preparations for rectal application, oleaginous suppositories and aqueous suppositories.

Various preparations may be prepared by addition of pharmacologically acceptable and commonly used diluents, binder, lubricant, disintegrator, surfactant, fluidizer, etc. thereto. Examples of the diluents include lactose, fructose, glucose, corn starch, sorbitol and crystalline cellulose; examples of the binder include methyl cellulose, ethyl cellulose, gum arabic, gelatin, hydroxypropyl cellulose and polyvinylpyrrolidone; examples of the lubricant include talc, magnesium stearate, polyethylene glycol and hydrogenated vegetable oil; examples of the disintegrator include starch, sodium alginate, gelatin, calcium carbonate, calcium citrate, dextrin, magnesium carbonate and synthetic magnesium silicate; examples of the surfactant include sodium laurylsulfate, soybean lecithin, sucrose fatty acid ester and Polysolvate 80; examples of the fluidizer include light anhydrous silicic acid, dried aluminum hydroxide gel, synthetic aluminum silicate and magnesium silicate; and examples of other excipients include syrup, vaseline, glycerin, ethanol, propylene glycol, citric acid, sodium chloride, sodium nitrite and sodium phosphate.

Dose of the compound of the present invention may be appropriately increased or decreased by taking dose regimen, age, sex, symptom in a patient, etc. into consideration and, may be generally administered in an amount of from 1 to 1,000 mg or, preferably, 5 to 300 mg, for adult, at ounce or in several divided administrations per day.

EXAMPLES

The present invention will now be illustrated by referring to Examples and the present invention is not limited to the following Examples.

Example 1-1

Synthesis of (E)-2-(dimethylamino)ethyl dec-2-enoate [Compound 1]

trans-2-Decenoic acid (170 mg, 1 mmol) and N,N-dimethylaminoethanol (90 mg, 1 mmol) were dissolved in anhydrous dichloromethane (10 ml) and, under stirring in an ice bath, N-(3-dimethylaminopropyl)-N'-ethylcarbodiimide hydrochloride (211 mg, 1.1 mmol) (Sigma-Aldrich) was added thereto. After stirring in an ice bath for 1 hour and then at room temperature for 8 hours, the reaction solution was poured over a diluted hydrochloric acid solution followed by extracting with chloroform. The chloroform layer was concentrated to give the aimed compound as a light brown oily product.

$C_4H_{27}NO_2$ MW 242, positive ion HR-FABMS m/z: 242.2118 [M+H]$^+$ (Calcd for $C_{14}H_{28}NO_2$: 242.2120), positive ion FABMS m/z: 242 [M+H]$^+$, $^1$H-NMR (400 MHz, CDCl$_3$) δ 0.88 (3H, t, J=6.8 Hz), 1.29 (8H, br s), 1.45 (2H, m), 2.19 (2H, m), 2.29 (6H, s), 2.60 (2H, t, J=5.9 Hz), 4.23 (2H, t, J=5.9 Hz), 5.85 (1H, dt, J=15.6, 1.5 Hz), 6.98 (1H, dt, J=15.6, 6.9 Hz).

Example 1-2

Synthesis of (E)-2-(dimethylamino)ethyl dec-2-enoate [Compound 1]

(Another Method)

Thionyl chloride (8 ml) was added to trans-2-decenoic acid (3.4 g, 0.02 mol) followed by refluxing on a hot water bath for 2 hours. An excessive thionyl chloride was evaporated in vacuo to give 2-decenoic acid chloride. Pyridine (1 ml) was added to a solution of N,N-dimethylaminoethanol (2.0 g, 0.022 mol) in tetrahydrofuran (30 ml) followed by dropping into a solution of 2-decenoic acid chloride in tetrahydrofuran (20 ml). The reaction solution was heated to reflux on a hot water bath for 3 hours, tetrahydrofuran was evaporated in vacuo, water and ethyl acetate were added to the residue to partition and an ethyl acetate layer was collected therefrom. The ethyl acetate layer was washed with water and evaporated followed by purifying by silica gel column chromatography (developer: chloroform) to give the aimed compound as a light brown oily product.

Spectral data thereof are the same as those in Example 1-1.

Example 2

(E)-3-(Dimethylamino)propyl dec-2-enoate [Compound 2]

The same operation as in Example 1-1 or 1-2 was carried out using trans-2-decenoic acid and 3-dimethylamino-1-propanol as starting materials to give the aimed compound.

Colorless oily product, $C_{14}H_{27}NO_2$ MW 255, HREIMS m/z: 255.2195 [M+H]$^+$ (Calcd for $C_{14}H_{27}NO_2$: 255.2198), EIMS m/z (rel. int.): 255 (M$^+$, 4), 153 (4), $^1$H-NMR (400 MHz, CDCl$_3$) δ: 0.88 (3H, t, J=6.8 Hz), 1.29 (8H, br s), 1.45 (2H, m), 1.83 (2H, m), 2.18 (2H, m), 2.24 (6H, s), 2.36 (2H, t, J=7.2 Hz), 4.16 (2H, t, J=6.6 Hz), 5.81 (1H, dt, J=16.0, 1.7 Hz), 6.96 (1H, dt, J=16.0, 7.0 Hz).

Example 3

(E)-1-(dimethylamino)propan-2-yl dec-2-enoate [Compound 3]

The same operation as in Example 1-1 or 1-2 was carried out using trans-2-decenoic acid and 1-dimethylamino-2-propanol as starting materials to give the aimed compound.

Light brown oily product, $C_{15}H_{30}NO_2$ MW 256, positive ion HR-FABMS m/z: 256.2284 [M+H]$^+$ (Calcd for $C_{15}H_{30}NO_2$: 256.2277), positive ion FABMS m/z: 256 [M+H]$^+$, $^1$H-NMR (400 MHz, CDCl$_3$) δ: 0.88 (3H, t, J=6.8 Hz), 1.22 (3H, d, J=10.0 Hz), 1.25 (8H, br s), 1.44 (2H, m), 2.18 (2H, m), 2.26 (6H, s), 2.31 (1H, dd, J=13.2, 5.2 Hz), 2.53

(1H, dd, J=13.2, 7.4 Hz), 5.10 (1H, m), 5.81 (1H, dt, J=15.8 Hz), 6.95 (1H, dt, J=15.8, 7.8 Hz).

Example 4

(E)-4-(dimethylamino)butyl dec-2-enoate [Compound 4]

The same operation as in Example 1-1 or 1-2 was carried out using trans-2-decenoic acid and 4-dimethylamino-1-butanol as starting materials to give the aimed compound.

Colorless oily product, $C_{16}H_{31}NO_2$ MW 269, HREIMS m/z: 269.2347 [M+H]$^+$ (Calcd for $C_{16}H_{31}NO_2$: 269.2355), EIMS m/z (rel. int.): 269 (M$^+$, 5), 116 (5), $^1$H-NMR (400 MHz, CDCl$_3$) δ 0.88 (3H, t, J=6.8 Hz), 1.29 (8H, br s), 1.45 (2H, m), 1.56 (2H, m), 1.68 (2H, m), 2.18 (2H, m), 2.23 (6H, s), 2.29 (2H, t, J=7.6 Hz), 4.14 (2H, t, J=6.4 Hz), 5.80 (1H, dt, J=15.8, 1.6 Hz), 6.96 (1H, dt, J=15.8, 7.0 Hz).

Example 5

(E)-3-(dimethylamino)-2,2-dimethylpropyl dec-2-enoate [Compound 5]

The same operation as in Example 1-1 or 1-2 was carried out using trans-2-decenoic acid and 3-dimethylamino-2,2-dimethyl-1-propanol as starting materials to give the aimed compound.

Colorless oily product, $C_{17}H_{33}NO_2$ MW 283, HREIMS m/z: 283.2506 [M+H]$^+$ (Calcd for $C_{17}H_{33}NO_2$: 283.2511), EIMS m/z (rel. int.): 283 (M$^+$, 2), 153 (2), $^1$H-NMR (400 MHz, CDCl$_3$) δ 0.87 (3H, t, J=7.0 Hz), 0.90 (6H, s), 1.28 (8H, br 5), 1.45 (2H, m), 2.16 (2H, s), 2.18 (2H, m), 2.26 (6H, s), 3.92 (2H, s), 5.81 (1H, dt, J=15.8 Hz), 6.94 (1H, dt, J=15.8, 6.8 Hz).

Example 6

(E)-2-(diethylamino)ethyl dec-2-enoate [Compound 6]

The same operation as in Example 1-1 or 1-2 was carried out using trans-2-decenoic acid and 2-(diethylamino)ethanol as starting materials to give the aimed compound.

Colorless oily product, $C_{16}H_{32}NO_2$ MW 270, positive ion HR-FABMS 270.2424 [M+H]$^+$ for (Calcd for $C_{16}H_{32}NO_2$: 270.2433), positive ion FABMS m/z: 270 [M+H]$^+$, $^1$H-NMR (400 MHz, CDCl$_3$) δ: 0.87 (3H, t, J=7.2 Hz), 1.04 (6H, t, J=7.3 Hz), 1.29 (8H, br s), 1.45 (2H, m), 2.19 (2H, m), 2.60 (4H, q, J=7.3 Hz), 2.74 (2H, t, J=6.3 Hz), 4.20 (2H, t, J=6.3 Hz), 5.83 (1H, dt, J=16.0 Hz), 6.97 (1H, dt, J=16.0, 7.8 Hz).

Example 7

(E)-6-(dimethylamino)hexyl dec-2-enoate [Compound 7]

The same operation as in Example 1-1 or 1-2 was carried out using trans-2-decenoic acid and 6-dimethylamino-1-hexanol as starting materials to give the aimed compound.

Oily product, $C_{18}H_{35}NO_2$ MW 297, HR-EIMS (positive ion mode): m/z 298.2761 [M+H]$^+$ (calcd for $C_{18}H_{35}NO_2$, 298.2741), $^1$H-NMR (500 MHz, CDCl$_3$) δ: 0.88 (3H, t, J=6.9 Hz), 1.29 (8H, m), 1.33 (4H, m), 1.44 (2H, m), 1.51 (2H, m), 1.68 (2H, m), 2.19 (2H, m), 2.27 (6H, s), 2.33 (2H, t, J=7.7 Hz), 4.11 (2H, t, J=6.6 Hz), 5.81 (1H, d, J=15.8 Hz), 6.96 (1H, dt, J=15.8, 7.0 Hz).

Example 8

(E)-2-(isopropylthio)ethyl dec-2-enoate [Compound 8]

The same operation as in Example 1-1 or 1-2 was carried out using trans-2-decenoic acid and 2-(isopropylthio)ethanol as starting materials to give the aimed compound.

Oily product, $C_{15}H_{28}O_2S$ MW 272, $^1$H-NMR (500 MHz, CDCl$_3$) δ: 0.88 (3H, t, J=6.6 Hz), 1.28 (8H, m), 1.28 (6H, d, J=6.6 Hz), 1.45 (2H, m), 2.20 (2H, m), 2.78 (2H, t, J=7.2 Hz), 3.00 (1H, m), 4.27 (2H, t, J=7.2 Hz), 5.82 (1H, d, J=14.6 Hz), 6.98 (1H, dt, J=14.6, 6.8 Hz).

Example 9

(E)-2-methoxyethyl dec-2-enoate [Compound 9]

The same operation as in Example 1-1 or 1-2 was carried out using trans-2-decenoic acid and methyl cellosolve as starting materials to give the aimed compound.

Oily product, $C_{13}H_{24}O_3$ MW 228, DART-MS: m/z 230 [M+2H]$^+$, $^1$H-NMR (500 MHz, CDCl$_3$) δ: 0.88 (3H, t, J=6.9 Hz), 1.26-1.31 (8H, m), 1.43-1.46 (2H, m), 2.20 (2H, dt, J=7.5, 6.9 Hz), 3.40 (3H, s), 3.63 (2H, m), 4.28 (2H, m), 5.86 (1H, d, J=15.8 Hz), 7.00 (1H, dt, J=15.8, 6.9 Hz).

Example 10

(E)-2-ethoxyethyl dec-2-enoate [Compound 10]

The same operation as in Example 1-1 or 1-2 was carried out using trans-2-decenoic acid and ethyl cellosolve as starting materials to give the aimed compound.

Oily product, $C_{14}H_{26}O_3$ MW 242, HR-ESIMS (positive ion mode): m/z 243.1961 [M+H]$^+$ (calcd for $C_{14}H_{27}O_3$, 243.1955), $^1$H-NMR (500 MHz, CDCl$_3$) δ: 0.88 (3H, t, J=6.9 Hz), 1.21-1.24 (3H, m) 1.27-1.30 (8H, m), 1.42-1.46 (2H, m), 2.17-2.22 (2H, dt, J=7.5, 6.9 Hz), 3.52-3.57 (2H, m), 3.65-3.67 (2H, m), 4.27-4.29 (2H, m), 5.86 (1H, d, J=16.1 Hz), 7.00 (1H, dt, J=16.1, 6.9 Hz).

Example 11

(E)-1,3-diethoxy-2-propyl dec-2-enoate [Compound 11]

The same operation as in Example 1-1 or 1-2 was carried out using trans-2-decenoic acid and 1,3-diethoxy-2-propanol as starting materials to give the aimed compound.

Oily product, $C_{17}H_{32}O_4$ MW 300, HR-ESIMS (positive ion mode): m/z 323.2193 (calcd for $C_{17}H_{32}O_4Na$, 323.2188), $^1$H-NMR (500 MHz, CDCl$_3$) δ: 0.87 (3H, m), 1.18 (6H, m), 1.27 (8H, m), 1.44 (2H, m), 2.19 (2H, m), 3.52 (4H, m), 3.60 (4H, m), 5.15 (1H, m), 5.86 (1H, m), 6.98 (1H, m).

Example 12

(E)-2-(2-(dimethylamino)ethoxy)ethyl dec-2-enoate [Compound 12]

The same operation as in Example 1-1 or 1-2 was carried out using trans-2-decenoic acid and 2-(2-(dimethylamino)ethoxy)ethanol as starting materials to give the aimed compound.

Colorless oily product, $C_{16}H_{31}NO_3$ MW 285, HREIMS m/z: 285.2298 [M+H]$^+$ for (Calcd for $C_{16}H_{31}NO_3$:

285.2304), EIMS m/z (rel. int.): 285 (M+, 2), 116 (5), ¹H-NMR (400 MHz, CDCl₃) δ: 0.88 (3H, t, J=6.8 Hz), 1.28 (8H, br s), 1.46 (2H, m), 2.20 (2H, m), 2.28 (6H, s), 2.54 (2H, t, J=5.3 Hz), 3.61 (2H, t, J=5.2 Hz), 3.70 (2H, t, J=5.2 Hz), 4.29 (2H, t, J=5.3 Hz), 5.85 (1H, dt, J=15.8 Hz), 7.00 (1H, dt, J=15.8 Hz).

Example 13

(E)-2-(2-(diethylamino)ethoxy)ethyl dec-2-enoate [Compound 13]

The same operation as in Example 1-1 or 1-2 was carried out using trans-2-decenoic acid and 2-(2-(diethylamino) ethoxy)ethanol as starting materials to give the aimed compound.

Light brown oily product, $C_{18}H_{35}NO_3$ MW 313, HREIMS m/z: 313.2614 [M+H]+ (Calcd for $C_{18}H_{35}NO_3$: 313.2617), EIMS m/z (rel. int.): 313 (M+, 2), 298 (2), ¹H-NMR (400 MHz, CDCl₃) δ: 0.88 (3H, t, J=6.6 Hz), 1.03 (6H, t, J=7.3 Hz), 1.28 (8H, br s), 1.44 (2H, m), 2.19 (2H, m), 2.57 (4H, q, J=7.3 Hz), 2.66 (2H, t, J=6.3 Hz), 3.58 (2H, t, J=6.3 Hz), 3.69 (2H, t, J=4.8 Hz), 4.28 (2H, t, J=4.8 Hz), 5.84 (1H, dt, J=16.0 Hz), 6.99 (1H, dt, J=16.0, 7.2 Hz).

Example 14

(E)-3-(2-(diethylamino)ethoxy)propyl dec-2-enoate [Compound 14]

The same operation as in Example 1-1 or 1-2 was carried out using trans-2-decenoic acid and 3-(2-(diethylamino) ethoxy)propan-1-ol as starting materials to give the aimed compound. Compound 14 was obtained by the purification using silica gel column chromatography.

Example 15

(E)-N-methyl dec-2-enamide [Compound 15]

The same operation as in Example 1-1 or 1-2 was carried out using trans-2-decenoic acid and methylamine as starting materials to give the aimed compound.

White powder, mp 60-63° C., $C_{11}H_{21}NO$, EIMS m/z 183 (M+) ¹H-NMR (CDCl₃, 500 MHz) δ 0.88 (3H, t, J=7.0 Hz), 1.22-1.33 (8H, m), 1.40-1.46 (2H, m), 2.14-2.19 (2H, m), 2.88 (3H, d, J=5.0 Hz), 5.41 (1H, brs), 5.72-5.76 (1H, m), 6.83 (1H, dt, J=15.3, 7.0 Hz).

Example 16

(E)-N-ethyl dec-2-enamide [Compound 16]

The same operation as in Example 1-1 or 1-2 was carried out using trans-2-decenoic acid and ethylamine as starting materials to give the aimed compound.

White powder, mp 38-40° C., $C_{12}H_{23}NO$, EIMS m/z=197 (M+) ¹H-NMR (CDCl₃, 500 MHz) δ: 0.88 (3H, t, J=7.0 Hz), 1.17 (3H, t, J=7.3 Hz), 1.23-1.32 (8H, m), 1.41-1.46 (2H, m), 2.14-2.19 (2H, m), 3.33-3.39 (2H, m), 5.40 (1H, brs), 5.71-5.75 (1H, m), 6.83 (1H, dt, J=15.3, 7.1 Hz).

Example 17

(E)-N-butyl dec-2-enamide [Compound 17]

The same operation as in Example 1-1 or 1-2 was carried out using trans-2-decenoic acid and butylamine as starting materials to give the aimed compound.

White powder, mp=31-32 $C_{14}H_{27}NO$, EIMS m/z 225 (M+) ¹H-NMR (CDCl₃, 500 MHz) δ 0.88 (3H, t, J=7.0 Hz), 0.93 (3H, t, J=7.4 Hz), 1.23-1.32 (8H, m), 1.32-1.40 (2H, m), 1.40-1.46 (2H, m), 1.48-1.54 (2H, m), 2.14-2.19 (2H, m), 3.30-3.34 (2H, m), 5.42 (1H, brs), 5.72-5.76 (1H, m), 6.83 (1H, dt, J=15.2, 7.0 Hz).

Example 18

(E)-N-isobutyl dec-2-enamide [Compound 18]

The same operation as in Example 1-1 or 1-2 was carried out using trans-2-decenoic acid and isobutylamine as starting materials to give the aimed compound.

White powder, mp 42-45° C., $C_{14}H_{27}NO$, EIMS m/z: 225 (M+) ¹H-NMR (CDCl₃, 500 MHz) δ: 0.88 (3H, t, J=7.0 Hz), 0.93 (6H, d, J=6.7 Hz), 1.23-1.32 (8H, m), 1.41-1.47 (2H, m), 1.74-1.84 (1H, m), 2.15-2.19 (2H, m), 3.14-3.17 (2H, m), 5.45 (1H, brs), 5.74-5.77 (1H, m), 6.84 (1H, dt, J=15.2, 7.0 Hz).

Example 19

(E)-N-pentyl dec-2-enamide [Compound 19]

The same operation as in Example 1-1 or 1-2 was carried out using trans-2-decenoic acid and amylamine as starting materials to give the aimed compound.

Oily product, $C_{15}H_{29}NO$ MW 239, HR-ESIMS (positive ion mode): m/z 240.2305 [M+H]+ (calcd for $C_{15}H_{30}NO$, 240.2322), ¹H-NMR (500 MHz, CDCl₃) δ: 0.86-0.93 (6H, m), 1.26-1.33 (12H, m), 1.41-1.45 (2H, m), 1.51-1.54 (2H, m), 2.14-2.19 (2H, m), 3.29-3.33 (2H, m), 5.76 (1H, d, J=15.2 Hz), 6.83 (1H, dt, J=15.2, 6.9 Hz).

Example 20

(E)-N-isopentyl dec-2-enamide [Compound 20]

The same operation as in Example 1-1 or 1-2 was carried out using trans-2-decenoic acid and isoamylamine as starting materials to give the aimed compound.

White powder, mp: 28-31° C., $C_{15}H_{29}NO$, EIMS m/z: 239 (M+) ¹H-NMR (CDCl₃, 500 MHz) δ: 0.88 (3H, t, J=7.0 Hz), 0.92 (6H, d, J=6.7 Hz), 1.23-1.32 (8H, m), 1.40-1.46 (4H, m), 1.59-1.67 (1H, m), 2.14-2.19 (2H, m), 3.32-3.36 (2H, m), 5.37 (1H, brs), 5.71-5.75 (1H, m), 6.82 (1H, dt, J=15.3, 7.1 Hz).

Example 21

(E)-N-tert-pentyl dec-2-enamide [Compound 21]

The same operation as in Example 1-1 or 1-2 was carried out using trans-2-decenoic acid and tert-amylamine as starting materials to give the aimed compound.

Oily product, $C_{15}H_{29}NO$ MW 239, HR-ESIMS (positive ion mode): m/z 240.2311 [M+H]+ (calcd for $C_{15}H_{30}NO$, 240.2322), ¹H-NMR (500 MHz, CDCl₃) δ 0.85 (3H, t, J=7.5 Hz), 0.87 (3H, t, J=6.9 Hz), 1.26-1.31 (8H, m), 1.32 (6H, s), 1.40-1.45 (2H, m), 1.74-1.78 (2H, m), 2.12-2.16 (2H, m), 5.70 (1H, d, J=14.9 Hz), 6.95 (1H, dt, J=14.9, 6.9 Hz).

Example 22

(E)-N-hexyl dec-2-enamide [Compound 22]

The same operation as in Example 1-1 or 1-2 was carried out using trans-2-decenoic acid and hexylamine as starting materials to give the aimed compound.

White powder, $C_{16}H_{31}NO$ MW 253, HR-ESIMS (positive ion mode): m/z 254.2468 [M+H]$^+$ (calcd for $C_{16}H_{32}NO$, 254.2478), $^1$H-NMR (500 MHz, CDCl$_3$) 0.86-0.89 (6H, m), 1.25-1.34 (14H, m), 1.41-1.45 (2H, m), 1.49-1.55 (2H, m), 2.14-2.18 (2H, m), 3.28-3.32 (2H, m), 5.76 (1H, d, J=15.2 Hz), 6.81 (1H, dt, J=15.2, 6.9 Hz).

Example 23

(E)-N-heptyl dec-2-enamide [Compound 23]

The same operation as in Example 1-1 or 1-2 was carried out using trans-2-decenoic acid and heptylamine as starting materials to give the aimed compound.

White powder, $C_{17}H_{33}NO$ MW 267, HR-ESIMS (positive ion mode): m/z 268.2627 [M+H]$^+$ (calcd for $C_{17}H_{34}NO$, 268.2635), $^1$H-NMR (500 MHz, CDCl$_3$) δ: 0.88 (6H, t, J=6.9 Hz), 1.27-1.31 (16H, m), 1.40-1.45 (2H, m), 1.49-1.53 (2H, m), 2.14-2.17 (2H, m), 3.28-3.32 (2H, m), 5.76 (1H, d, J=14.2 Hz), 6.82 (1H, dt, J=14.2, 6.9 Hz).

Example 24

(E)-N-(heptan-4-yl) dec-2-enamide [Compound 24]

The same operation as in Example 1-1 or 1-2 was carried out using trans-2-decenoic acid and 4-heptylamine as starting materials to give the aimed compound.

Oily product, $C_{17}H_{33}NO$ MW 267, HR-ESIMS (positive ion mode): m/z 268.2626 [M+H]$^+$ (calcd for $C_{17}H_{34}NO$, 268.2635), $^1$H-NMR (500 MHz, CDCl$_3$) δ: 0.88 (3H, t, J=7.4 Hz), 0.90 (6H, t, J=7.4 Hz), 1.33 (12H, m), 1.46 (4H, m), 1.74 (2H, m), 2.16 (2H, dt, J=6.9 Hz), 4.02 (1H, br s), 5.16 (1H, br s), 5.74 (1H, d, J=14.6 Hz), 6.82 (1H, dt, J=14.6, 6.9 Hz).

Example 25

(E)-N-(octan-3-yl) dec-2-enamide [Compound 25]

The same operation as in Example 1-1 or 1-2 was carried out using trans-2-decenoic acid and 2-ethylhexylamine as starting materials to give the aimed compound.

Oily product, $C_{18}H_{35}NO$ MW 281, HR-ESIMS (positive ion mode): m/z 282.2778 [M+H]$^+$ (calcd for $C_{18}H_{36}NO$, 282.2791), $^1$H-NMR (500 MHz, CDCl$_3$) δ: 0.88 (3H, t, J=7.5 Hz), 0.90 (6H, t, J=7.5 Hz), 1.32 (16H, m), 1.44 (4H, m) 2.16 (2H, dt, J=6.9 Hz), 3.26 (1H, m), 5.40 (1H, br s), 5.75 (1H, d, J=14.9 Hz), 6.82 (1H, dt, J=14.9, 6.9 Hz).

Example 26

(E)-N-(2,4,4-trimethylpentan-2-yl) dec-2-enamide [Compound 26]

The same operation as in Example 1-1 or 1-2 was carried out using trans-2-decenoic acid and 1,1,3,3-tetramethylbutylamine as starting materials to give the aimed compound.

Oily product, $C_{18}H_{35}NO$ MW 281, HR-ESIMS (positive ion mode): m/z 282.2778 [M+H]$^+$ (calcd for $C_{18}H_{36}NO$, 282.2791), $^1$H-NMR (500 MHz, CDCl$_3$) δ: 0.88 (3H, t, J=7.0 Hz), 1.00 (9H, s), 1.28 (8H, m), 1.43 (6H, s), 1.67 (2H, m), 1.78 (2H, s), 2.14 (2H, dt, J=6.9 Hz), 5.24 (1H, br s), 5.66 (1H, d, J=14.9 Hz), 6.75 (1H, dt, J=14.9, 6.9 Hz).

Example 27

(E)-N-cyclohexyl dec-2-enamide [Compound 27]

The same operation as in Example 1-1 or 1-2 was carried out using trans-2-decenoic acid and cyclohexylamine as starting materials to give the aimed compound.

White powder, mp 94-96° C., $C_{16}H_{29}NO$, EIMS m/z: 251 (M$^+$) $^1$H-NMR (CDCl$_3$, 500 MHz) δ 0.88 (3H, t, J=7.0 Hz), 1.09-1.21 (3H, m), 1.23-1.32 (8H, m), 1.34-1.46 (4H, m), 1.59-1.74 (3H, m), 1.92-1.97 (2H, m), 2.13-2.18 (2H, m), 3.80-3.88 (1H, m), 5.23-5.31 (1H, m), 5.70-5.73 (1H, m), 6.81 (1H, dt, J=15.3, 7.0 Hz).

Example 28

(E)-N-phenyl dec-2-enamide [Compound 28]

The same operation as in Example 1-1 or 1-2 was carried out using trans-2-decenoic acid and aniline as starting materials to give the aimed compound.

Yellowish-white powder, mp 54-55° C., $C_{16}H_{23}N_4$, EIMS m/z 245 (M$^+$) $^1$H-NMR (CDCl$_3$, 500 MHz) δ 0.89 (3H, t, J=7.0 Hz), 1.23-1.36 (8H, m), 1.45-1.51 (2H, m), 2.21-2.26 (2H, m), 5.89-5.93 (1H, m), 7.00 (1H, dt, J=15.2, 7.1 Hz), 7.09-7.15 (2H, m), 7.33 (2H, m), 7.53-7.60 (2H, m).

Example 29

(E)-N-phenethyl dec-2-enamide [Compound 29]

The same operation as in Example 1-1 or 1-2 was carried out using trans-2-decenoic acid and 2-phenylethaneamine as starting materials to give the aimed compound. Compound 29 was obtained by the purification using silica gel column chromatography.

Example 30

(E)-N-(2-pyrrolidin-1-ylethyl) dec-2-enamide [Compound 30]

The same operation as in Example 1-1 or 1-2 was carried out using trans-2-decenoic acid and 1-(2-aminoethyl)pyrrolidine as starting materials to give the aimed compound.

Light orange powder, mp=56-58° C., $C_{16}H_{30}N_2O$, EIMS m/z (%): 266 (M$^+$) $^1$H-NMR (CDCl$_3$, 500 MHz) δ: 0.88 (3H, t, J=7.0 Hz), 1.22-1.32 (8H, m), 1.41-1.47 (2H, m), 1.78-1.83 (4H, m), 2.14-2.18 (2H, m), 2.53-2.58 (4H, m), 2.65 (2H, t, J=5.9 Hz), 3.42-3.46 (2H, m), 5.78-5.82 (1H, m), 6.22 (1H, brs), 6.84 (1H, dt, J=15.3, 7.0 Hz).

Example 31

(E)-N,N-diethyl dec-2-enamide [Compound 31]

The same operation as in Example 1-1 or 1-2 was carried out using trans-2-decenoic acid and diethylamine as starting materials to give the aimed compound.

Colorless oily product, $C_{14}H_{27}NO$ MW 225, EIMS m/z: 225 (M$^+$, 21), 196 (5), 182 (5), 168 (5), 153 (35), 140 (6), 126 (100), 100 (6), 83 (6), 69 (13), 58 (27).

Example 32

(E)-N,N-dibutyl dec-2-enamide [Compound 32]

The same operation as in Example 1-1 or 1-2 was carried out using trans-2-decenoic acid and dibutylamine as starting materials to give the aimed compound.

Oily product, $C_{18}H_{35}NO$ MW 281, HR-ESIMS (positive ion mode): m/z 282.2780 [M+H]$^+$ (calcd for $C_{18}H_{36}NO$, 282.2791), $^1$H-NMR (500 MHz, CDCl$_3$) δ: 0.88 (3H, t, J=6.9 Hz), 0.92 (3H, t, J=7.4 Hz), 0.95 (3H, t, J=7.4 Hz), 1.32 (14H, m), 1.45 (2H, m), 1.54 (4H, m), 2.19 (2H, dt, J=6.9 Hz), 3.28 (2H, t, J=7.5 Hz), 3.36 (2H, t, J=7.5 Hz), 6.18 (1H, d, J=14.9 Hz), 6.89 (1H, dt, J=14.9, 6.9 Hz).

Example 33

(E)-N,N-dipentyl dec-2-enamide [Compound 33]

The same operation as in Example 1-1 or 1-2 was carried out using trans-2-decenoic acid and diamylamine as starting materials to give the aimed compound.

Oily product, $C_{20}H_{39}NO$ MW 309, HR-ESIMS (positive ion mode): m/z 310.3097 [M+H]$^+$ (calcd for $C_{20}H_{40}NO$, 310.3104), $^1$H-NMR (500 MHz, CDCl$_3$) δ: 0.85-0.95 (9H, m), 1.25-1.39 (16H, m), 1.45 (2H, m), 1.56 (2H, m), 2.20 (2H, m), 3.28 (2H, m), 3.35 (2H, m), 6.18 (1H, d, J=14.9 Hz), 6.90 (1H, dt, J=14.9, 7.3 Hz).

Example 34

(E)-N,N-dihexyl dec-2-enamide [Compound 34]

The same operation as in Example 1-1 or 1-2 was carried out using trans-2-decenoic acid and dihexylamine as starting materials to give the aimed compound.

Oily product, $C_{22}H_{43}NO$ MW 337, HR-ESIMS (positive ion mode): m/z 338.3421 [M+H]$^+$ (calcd for $C_{22}H_{44}NO$, 338.3417), $^1$H-NMR (500 MHz, CDCl$_3$) δ 0.89 (9H, m), 1.23-1.34 (20H, m), 1.44 (2H, m), 1.55 (4H, m), 2.19 (2H, m), 3.29 (2H, t, J=7.4 Hz), 3.34 (2H, t, J=7.4 Hz), 6.18 (1H, m), 6.90 (1H, m).

Example 35

(E)-N-ethyl-N-heptyl dec-2-enamide [Compound 35]

The same operation as in Example 1-1 or 1-2 was carried out using trans-2-decenoic acid and N-ethyl-N-heptylamine as starting materials to give the aimed compound.

Oily product, $C_{19}H_{37}NO$ MW 295 HR-ESIMS (positive ion mode) m/z 296.2934 [M+H]$^+$ (calcd for $C_{19}H_{37}NO$, 296.2948), $^1$H-NMR (500 MHz, CDCl$_3$) δ: 0.88 (6H, m), 1.14 (1H, t, J=6.9 Hz), 1.18 (1H, t, J=6.9 Hz), 1.23-1.34 (17H, m), 1.45 (2H, m), 1.56 (2H, m), 2.19 (2H, m), 3.27 (1H, t, J=7.7 Hz), 3.36 (2H, m), 3.42 (1H, m), 6.17 (1H, d, J=15.3 Hz), 6.89 (1H, dt, J=15.3, 6.7 Hz).

Example 36

(E)-N-2-(dimethylamino)ethyl dec-2-enamide [Compound 36]

The same operation as in Example 1-1 or 1-2 was carried out using trans-2-decenoic acid and N,N-dimethylethane-1,2-diamine as starting materials to give the aimed compound.

Colorless oily product, $C_{14}H_{28}N_2O$ MW 240, positive ion HR-FABMS m/z: 241.2284 [M+H]$^+$ (Calcd for $C_{14}H_{29}N_2O$: 241.2280), positive ion FABMS: m/z 241 [M+H]$^+$, DART-MS m/z: 241.2 [M+H]$^+$, $^1$H-NMR (400 MHz, CDCl$_3$) δ 0.88 (3H, t, J=6.8 Hz), 1.28 (8H, hr s), 1.43 (2H, m), 2.14 (2H, m), 2.23 (6H, s), 2.43 (2H, t, J=5.8 Hz), 3.40 (2H, t, J=5.8 Hz), 5.79 (1H, dt, J=15.6 Hz), 6.17 (1H of NH), 6.82 (1H, dt, J=15.6, 7.2 Hz).

Example 37

(E)-N-2-(diethylamino)ethyl dec-2-enamide [Compound 37]

The same operation as in Example 1-1 or 1-2 was carried out using trans-2-decenoic acid and N,N-diethylethane-1,2-diamine as starting materials to give the aimed compound.

Colorless oily product, $C_{16}H_{32}N_2O$ MW 268, positive ion HR-FABMS m/z: 269.2602 [M+H]$^+$ (Calcd for $C_{16}H_{33}N_2O$: 269.2593), positive ion FABMS m/z: 269 [M+H]$^+$, $^1$H-NMR (400 MHz, CDCl$_3$) δ=0.89 (3H, t, J=6.8 Hz), 1.01 (6H, t, J=7.1 Hz), 1.28 (8H, br s), 1.43 (2H, m), 2.16 (2H, m), 2.54 (4H, q, J=7.1 Hz), 2.56 (2H, t, J=7.6 Hz), 3.36 (2H, t, J=7.6 Hz), 5.79 (1H, dt, J=15.4 Hz), 6.26 (1H of NH), 6.81 (1H, dt, J=15.4, 7.6 Hz).

Example 38

(E)-N-3-(dimethylamino)propyl dec-2-enamide [Compound 38]

The same operation as in Example 1-1 or 1-2 was carried out using trans-2-decenoic acid and N,N-dimethylpropane-1,3-diamine as starting materials to give the aimed compound.

Brown oily product, $C_{15}H_{30}N_2O$ MW 254, HR-IT-TOFMS m/z: 255.2455 [M+H]$^+$ (Calcd for $C_{15}H_{31}N_2O$: 255.2431), $^1$H-NMR (500 MHz, CDCl$_3$) δ 0.88 (3H, t, J=6.9 Hz, H-10'), 1.28 (8H, m, H-6'-9'), 1.43 (2H, quin, J=6.9 Hz, H-5'), 1.69 (2H, quin, J=6.3 Hz, H-3), 2.16 (2H, ddt, J=7.5, 7.2, 1.5 Hz, H-4'), 2.25 (6H, s, H-6, 7), 2.41 (2H, t, J=6.3 Hz, H-4), 3.40 (2H, dt, J=6.3, 5.8 Hz, H-2), 5.73 (1H, dt, J=15.2, 1.5 Hz, H-2'), 6.77 (1H, dt, J=15.2, 6.9 Hz, H-3'), 6.98 (1H, br s, H-1).

Example 39

(E)-N-3-(diethylamino)propyl dec-2-enamide [Compound 39]

The same operation as in Example 1-1 or 1-2 was carried out using trans-2-decenoic acid and N,N-diethylpropane-1,3-diamine as starting materials to give the aimed compound.

Brown oily product, $C_{17}H_{24}N_2O$ MW 296, HR-IT-TOFMS m/z: 297.2935 [M+H]$^+$ (Calcd for $C_{17}H_{25}N_2O$: 297.2900), $^1$H-NMR (500 MHz, CDCl$_3$) δ 0.88 (3H, t, J=6.9 Hz, H-10'), 1.05 (6H, t, J=7.3 Hz, H-7, 9), 1.28 (8H, m, H-6'-9'), 1.43 (2H, quin, J=7.1 Hz, H-5'), 1.67 (2H, quin, J=6.1 Hz, H-3), 2.15 (2H, dt, J=7.3, 7.3 Hz, H-4'), 2.53 (6H, quin, J=6.7 Hz, H-4, 6, 8), 3.41 (2H, dd, J=11.5, 5.4 Hz, H-2), 5.71 (1H, d, J=15.3 Hz, H-2'), 6.76 (1H, quin, J=7.3 Hz, H-3'), 7.59 (1H, br s, H-1).

Example 40

(E)-N-2-(diisopropylamino)ethyl dec-2-enamide [Compound 40]

The same operation as in Example 1-1 or 1-2 was carried out using trans-2-decenoic acid and N,N-diisopropylethane-1,2-diamine as starting materials to give the aimed compound.

Brown oily product, $C_{18}H_{36}N_2O$ MW 296, HR-IT-TOFMS m/z: 297.2935 [M+H]$^+$ (Calcd for $C_{18}H_{37}N_2O$: 297.2935), $^1$H-NMR (500 MHz, CDCl$_3$) δ 0.88 (3H, t, J=6.9 Hz, H-10'), 1.02 (12H, d, J=6.1 Hz, H-6, 7, 9, 10), 1.28 (8H, m, H-6'-9'), 1.43 (2H, quin, J=7.3 Hz, H-5'), 2.16 (2H, ddt, J=6.9, 6.9, 1.5 Hz, H-4'), 2.61 (2H, t, J=5.7 Hz, H-3), 3.02 (2H, sext, J=6.6 Hz, H-5, 8), 3.29 (2H, dd, J=10.7, 5.4 Hz, H-2), 5.74 (1H, d, J=15.3 Hz, H-2'), 6.79 (1H, quin, J=7.3 Hz, H-3').

Example 41

(E)-N-2-(dibutylamino)ethyl dec-2-enamide [Compound 41]

The same operation as in Example 1-1 or 1-2 was carried out using trans-2-decenoic acid and N,N-dibutylethane-1,2-diamine as starting materials to give the aimed compound.

Brown oily product, $C_{20}H_{40}N_2O$ MW 324, HR-IT-TOFMS m/z: 325.3244 [M+H]$^+$ (Calcd for $C_{20}H_{41}N_2O$: 325.3213), $^1$H-NMR (500 MHz, CDCl$_3$) δ 0.88 (3H, t, J=6.9 Hz, H-10'), 0.91 (6H, t, J=7.3 Hz, H-8, 12), 1.29 (12H, m, H-7, 11, 6'-9'), 1.40 (6H, m, H-6, 10, 5'), 2.17 (2H, ddt, J=7.1, 7.1, 1.5 Hz, H-4'), 2.42 (4H, t, J=7.3 Hz, H-5, 9), 2.54 (2H, t, J=5.7 Hz, H-3), 3.34 (2H, dd, J=11.5, 5.7 Hz, H-2), 5.76 (1H, dt, J=15.3, 1.5 Hz, H-2'), 6.16 (1H, br s, H-1), 6.80 (1H, dt, J=6.9 Hz, H-3').

Example 42

(E)-N-(2-(dimethylamino)ethyl)-N-methyl dec-2-enamide [Compound 42]

The same operation as in Example 1-1 or 1-2 was carried out using trans-2-decenoic acid and N,N',N'-trimethylethylenediamine as starting materials to give the aimed compound.

Oily product, $C_{15}H_{30}N_2O$ MW 254, HR-ESIMS (positive ion mode): m/z 255.2433 [M+H]$^+$ (calcd for $C_{15}H_{31}N_2O$, 255.2431), $^1$H-NMR (500 MHz, CDCl$_3$) δ: 0.88 (3H, t, J=6.9 Hz), 1.27-1.30 (8H, m), 1.45 (2H, quint, J=6.9 Hz), 2.20 (2H, dt, J=6.9, 13.8 Hz), 2.28 (6H, s), 2.49 (2H, t, J=7.5 Hz), 3.09 (3H, s), 3.55 (2H, t, J=6.9 Hz), 6.23 (1H, d, J=15.2 Hz), 6.89 (1H, dt, J=6.9, 15.2 Hz).

Example 43

(E)-N-(2-(dimethylamino)ethyl)-N-ethyl dec-2-enamide [Compound 43]

The same operation as in Example 1-1 or 1-2 was carried out using trans-2-decenoic acid and N-ethyl-N',N'-dimethylethylenediamine as starting materials to give the aimed compound.

Oily product, $C_{16}H_{32}N_2O$ MW 268, HR-ESIMS (positive ion mode): m/z 269.2597 [M+H]$^+$ (calcd for $C_{16}H_{33}N_2O$, 269.2587), $^1$H-NMR (500 MHz, CDCl$_3$) δ=0.88 (3H, t, J=7.5 Hz), 1.19 (3H, t, J=6.9 Hz), 1.27-1.30 (8H, m), 1.45 (2H, quint, J=7.5 Hz), 2.19 (2H, dt like q, J=6.9, 7.5 Hz), 2.32 (6H, s), 2.54 (2H, t, J=7.4 Hz), 3.90-3.54 (4H, m), 6.19 (1H, d, J=14.9 Hz), 6.91 (1H, dt, J=6.9, 14.9 Hz).

Example 44

(E)-N-(2-(diethylamino)ethyl)-N-ethyl dec-2-enamide [Compound 44]

The same operation as in Example 1-1 or 1-2 was carried out using trans-2-decenoic acid and N,N',N'-triethylethylenediamine as starting materials to give the aimed compound.

Oily product, $C_{18}H_{36}N_2O$ MW 296, HR-ESIMS (positive ion mode): m/z 297.2912 [M+H]$^+$ (calcd for $C_{18}H_{37}N_2O$, 297.2900), $^1$H-NMR (500 MHz, CDCl$_3$) δ: 0.88 (3H, t, J=6.9 Hz), 1.05 (6H, t, J=7.5 Hz), 1.20 (3H, t, J=7.5 Hz), 1.26-1.31 (8H, m), 1.45 (2H, quint, J=6.9 Hz), 2.20 (2H, dt like q, J=7.5 Hz), 2.53-2.64 (6H, m), 3.37-3.47 (4H, m), 6.19 (1H, d, J=14.9 Hz), 6.91 (1H, d, J=14.9, 7.5 Hz).

Example 45

(E)-N,N-bis(2-(dimethylamino)ethyl) dec-2-enamide [Compound 45]

The same operation as in Example 1-1 or 1-2 was carried out using trans-2-decenoic acid and N-(2-(dimethylamino)ethyl)-N',N' dimethylethane-1,2-diamine as starting materials to give the aimed compound.

Oily product, $C_{18}H_{37}N_3O$ MW 311, HR-ESIMS (positive ion mode): m/z 312.2997 [M+H]$^+$ (calcd for $C_{18}H_{38}N_3O$, 312.3009), $^1$H-NMR (500 MHz, CDCl$_3$) δ: 0.88 (3H, t, J=6.9 Hz), 1.26-1.31 (8H, m), 1.45 (2H, quint, J=6.9 Hz), 2.19 (2H, dt like q, J=6.9 Hz), 2.28 (12H, s), 2.46 (2H, t, J=7.4 Hz), 2.49 (2H, t, J=7.5 Hz), 3.47 (2H, t, J=7.5 Hz), 3.51 (2H, t, J=7.5 Hz), 6.20 (1H, d, J=15.2 Hz), 6.92 (1H, dt, J=6.9, 15.2 Hz).

Example 46

(E)-N,N-bis(2-(diethylamino)ethyl) dec-2-enamide [Compound 46]

The same operation as in Example 1-1 or 1-2 was carried out using trans-2-decenoic acid and N-(2-(diethylamino)ethyl)-N',N' diethylethane-1,2-diamine as starting materials to give the aimed compound.

Oily product, $C_{22}H_{45}N_3O$ MW 367, HR-ESIMS (positive ion mode): m/z 368.3640 [M+H]$^+$ (calcd for $C_{22}H_{46}N_3O$, 368.3635), $^1$H-NMR (500 MHz, CDCl$_3$) δ: 0.88 (3H, t, J=6.9 Hz), 1.04 (6H, t, J=7.5 Hz), 1.04 (6H, t, J=7.5 Hz), 1.26-1.31 (8H, m), 1.45 (2H, quint, J=6.9 Hz), 2.19 (2H, dt like q, J=7.6, 7.8 Hz), 2.53-2.64 (8H, m), 3.45 (4H, t, J=7.5 Hz), 3.47 (4H, t, J=7.5 Hz), 6.23 (1H, d, J=14.9 Hz), 6.91 (1H, dt, J=6.9, 14.9 Hz).

Example 47

(E)-N,N-bis(3-(dimethylamino)propyl) dec-2-enamide [Compound 47]

The same operation as in Example 1-1 or 1-2 was carried out using trans-2-decenoic acid and N-(3-(dimethylamino)propyl)-N',N'-dimethylpropane-1,3-diamine as starting materials to give the aimed compound.

Oily product, $C_{20}H_{41}N_3O$ MW 339, HR-ESIMS (positive ion mode): m/z 340.3301 [M+H]$^+$ (calcd for $C_{20}H_{42}N_3O$, 340.3322), $^1$H-NMR (500 MHz, CDCl$_3$) δ 0.88 (3H, t, J=6.9 Hz), 1.22-1.30 (8H, m), 1.45 (2H, q, J=6.9 Hz), 1.74 (4H, quint, J=7.5 Hz), 2.19 (2H, dt like q, J=6.9, 6.9 Hz), 2.22 (6H, s), 2.25 (6H, s), 2.27 (2H, t, J=6.9 Hz), 2.33 (2H, t, J=6.9 Hz), 3.39 (2H, t, J=7.5 Hz), 3.40 (2H, t, J=7.5 Hz), 6.27 (1H, d, J=14.9 Hz), 6.91 (1H, dt, J=6.9, 14.9 Hz).

Example 48

(E)-S-pentyl dec-2-enethioate [Compound 48]

The same operation as in Example 1-1 or 1-2 was carried out using trans-2-decenoic acid and 1-pentanethiol as starting materials to give the aimed compound.

Oily product, $C_{15}H_{28}OS$ MW 256, DART-MS: m/z 258 [M+2H]$^+$, $^1$H-NMR (500 MHz, CDCl$_3$) δ 0.89 (3H, t, J=6.9 Hz), 0.90 (3H, t, J=6.9 Hz), 1.20-1.40 (12H, m), 1.46 (2H, m), 1.60 (2H, m), 2.18 (2H, m), 2.93 (2H, t, J=6.9 Hz), 6.10 (1H, d, J=15.5 Hz), 6.89 (1H, dt, J=15.5, 6.9 Hz).

Example 49

(E)-S-isopentyl dec-2-enethioate [Compound 49]

The same operation as in Example 1-1 or 1-2 was carried out using trans-2-decenoic acid and isoamylmercaptan as starting materials to give the aimed compound.

Oily product, $C_{15}H_{28}OS$ MW 256, DART-MS: m/z 256 [M]$^+$, $^1$H-NMR (500 MHz, CDCl$_3$) δ 0.88 (3H, t, J=5.7 Hz), 0.92 (6H, d, J=6.3 Hz), 1.28 (8H, m), 1.47 (4H, m), 1.66 (1H, m), 2.18 (2H, m), 2.93 (2H, t, J=7.4 Hz), 6.10 (1H, d, J=16.3 Hz), 6.88 (1H, dt, J=16.3, 6.9 Hz).

Example 50

(E)-S-hexyl dec-2-enethioate [Compound 50]

The same operation as in Example 1-1 or 1-2 was carried out using trans-2-decenoic acid and n-hexylmercaptan as starting materials to give the aimed compound.

Oily product, $C_{16}H_{30}OS$ MW 270, DART MS: m/z 272 [M+2H]$^+$, $^1$H-NMR (500 MHz, CDCl$_3$) 0.88 (6H, t, J=6.9 Hz), 1.27-1.31 (12H, m), 1.38 (2H, m), 1.45 (2H, m), 1.60 (2H, m), 2.17 (2H, dt, J=7.5, 6.9 Hz), 2.93 (2H, t, J=7.2 Hz), 6.10 (1H, d, J=15.5 Hz), 6.89 (1H, dt, J=15.5, 6.9 Hz).

Example 51

(E)-S-heptyl dec-2-enethioate [Compound 51]

The same operation as in Example 1-1 or 1-2 was carried out using trans-2-decenoic acid and 1-heptanethiol as starting materials to give the aimed compound.

Oily product, $C_{17}H_{32}OS$ MW 284, DART-MS: m/z 286 [M+2H]$^+$, $^1$H-NMR (500 MHz, CDCl$_3$) δ: 0.88 (6H, t, J=6.9 Hz), 1.27-1.31 (12H, m), 1.38 (2H, m), 1.45 (2H, m), 1.60 (2H, m), 2.17 (2H, dt, J=7.5, 6.9 Hz), 2.93 (2H, t, J=7.2 Hz), 6.10 (1H, d, J=15.5 Hz), 6.89 (1H, dt, J=15.5, 6.9 Hz).

Example 52

(E)-S-decyl dec-2-enethioate [Compound 52]

The same operation as in Example 1-1 or 1-2 was carried out using trans-2-decenoic acid and 1-decanethiol as starting materials to give the aimed compound.

$C_{20}H_{38}OS$ MW 326, DART-MS: m/z 328 [M+2H]$^+$, $^1$H-NMR (500 MHz, CDCl$_3$) δ: 0.88 (6H, t, J=7.2 Hz), 1.26 (20H, br s), 1.36 (2H, m), 1.46 (2H, m), 1.59 (2H, tt, J=7.5 Hz), 2.18 (2H, dt, J=7.5, 6.9 Hz), 2.93 (2H, t, J=7.5 Hz), 6.10 (1H, d, J=15.5 Hz), 6.89 (1H, dt, J=15.5, 6.9 Hz).

Example 53

(E)-S-cyclopentyl dec-2-enethioate [Compound 53]

The same operation as in Example 1-1 or 1-2 was carried out using trans-2-decenoic acid and cyclopentanethiol as starting materials to give the aimed compound.

Oily product, $C_{15}H_{20}OS$ MW 254, DART-MS: m/z 256 [M+2H]$^+$, $^1$H-NMR (500 MHz, CDCl$_3$) δ: 0.88 (3H, t, J=6.9 Hz), 1.28 (8H, m), 1.45 (2H, m), 1.56 (2H, m), 1.63 (2H, m), 1.71 (2H, m), 2.11 (2H, dt, J=7.4, 5.7 Hz), 2.18 (2H, dt, J=7.5, 6.9 Hz), 3.78 (1H, tt, J=7.4 Hz), 6.07 (1H, d, J=15.5 Hz), 6.86 (1H, dt, J=15.5, 6.9 Hz).

Example 54

(E)-S-phenethyl dec-2-enethioate [Compound 54]

The same operation as in Example 1-1 or 1-2 was carried out using trans-2-decenoic acid and 2-phenylethanethiol as starting materials to give the aimed compound.

Oily product, $C_{18}H_{26}OS$ MW 290, DART-MS: m/z 290 [M]$^+$, $^1$H-NMR (500 MHz, CDCl$_3$) δ 0.88 (3H, t, J=6.9 Hz), 1.29 (8H, m) 1.46 (2H, m), 2.18 (2H, m), 2.89 (2H, t, J=7.7 Hz), 3.18 (2H, t, J=7.7 Hz), 6.10 (1H, d, J=15.2 Hz), 6.98 (1H, dt, J=15.2, 6.8 Hz).

Example 55

(E)-S-2-(dimethylamino)ethyl dec-2-enethioate [Compound 55]

The same operation as in Example 1-1 or 1-2 was carried out using trans-2-decenoic acid and 2-(dimethylamino) ethanethiol as starting materials to give the aimed compound.

Light brown oily product, $C_{14}H_{27}NOS$ MW 257, positive ion HR-FABMS m/z: 258.1895 [M+H]$^+$ (Calcd for $C_{14}H_{28}NOS$: 258.1892), positive ion FABMS m/z: 258 [M+H]$^+$, $^1$H-NMR (400 MHz, CDCl$_3$) δ 0.88 (3H, t, J=6.4 Hz), 1.29 (8H, br s), 1.45 (2H, m), 2.19 (2H, m), 2.34 (6H, s), 2.59 (2H, t, J=7.5 Hz), 3.09 (2H, t, J=7.5 Hz), 6.10 (1H, dt, J=15.6 Hz), 6.90 (1H, dt, J=15.6, 7.6 Hz).

Example 56

(E)-S-2-(diethylamino)ethyl dec-2-enethioate [Compound 56]

The same operation as in Example 1-1 or 1-2 was carried out using trans-2-decenoic acid and 2-(diethylamino) ethanethiol as starting materials to give the aimed compound.

Light brown oily product, $C_{16}H_{31}NOS$ MW 285, positive ion HR-FABMS m/z: 286.2198 [M+H]$^+$ (Calcd for $C_{16}H_{32}NOS$: 286.2205), positive ion FABMS m/z: 286 [M+H]$^+$, $^1$H-NMR (400 MHz, CDCl$_3$) δ: 0.88 (3H, t, J=5.6 Hz), 1.15 (6H, t, J=7.3 Hz), 1.28 (8H, br s), 1.45 (2H, m), 2.18 (2H, m), 2.80 (4H, q, J=7.3 Hz), 2.82 (2H, m), 3.11 (2H, t, J=8.2 Hz) 5.83 (1H, dt, J=15.6 Hz), 6.89 (1H, dt, J=7.8 Hz).

Test Example 1

Evaluation of Activation (Phosphorylation) of MAP Kinase

With regard to the compound 1 ((E)-2-(dimethylamino)-ethyl dec-2-enoate), activation of MAP kinase was measured as follows by a Western immunoblotting.

Nerve cells were dispersed from cerebral cortex of a fetal rat of 17 days age and said nerve cells were cultured for one day in a Dulbecco-modified Eagle medium (DMEM) containing 5% fetal bovine serum. The culture medium was exchanged with a serum-free medium (B27 supplement-added Neurobasal; Invitrogen) and the nerve cells were cultured at the density of 20,000 to 40,000 cells per cm$^2$ in a culture dish coated with polyornithine.

After three days, the compound 1 was added and the culture was continued for 30 minutes. After that, the cells were recovered on ice using a solution containing a phosphatase inhibitor where Tris-HCl buffer was a base. Protein concentration of the resulting cell extract was quantified using a BCA Protein Assay Kit (Takara Bio KK) and a certine amount of protein (3 μg for the measurement of MAP kinase and 5 μg for the measurement of phosphorylated MAP kinase) was subjected to polyacrylamide gel electrophoresis. The protein was transcribed from the gel after the electrophoresis to a PVDF membrane and a Western immunoblotting was carried out using each of an anti-MAP kinase antibody (Cell Signaling Technology) and an anti-phosphorylated MAP kinase antibody (Cell Signaling Technology) of the primary antibody.

After that, the reaction with an alkaline phosphatase-labeled anti-rabbit IgG antibody (Promega) of the secondary antibody was carried out so that the enzymatic activity was colorized whereupon the MAP kinase and the phosphorylated MAP kinase were measured.

Incidentally, the compound 1 was adjusted to the concentrations of 10 μg/ml, 30 μg/ml, 100 μg/ml and 300 μg/ml by dissolving in 0.1% DMSO. With regard to the control, 0.1% DMSO was added.

Intensity of the concentration of the above-obtained band of the gel subjected to electrophoresis was calculated and quantified using Image J (K. K. Bioarts). The numerical value for the MAP kinase using the compound 1 was divided by the numerical value for the MAP kinase of the control and, further, the numerical value for the phosphorylated MAP kinase using the compound 1 was divided by the numerical value for the phosphorylated MAP kinase of the control whereupon the ratio of the MAP kinase using the compound 1 to the control and the ratio of the phosphorylated kinase using the compound 1 to the control were determined.

After that, the resulting ratio of the phosphorylated MAP kinase to the control was divided by the resulting ratio of the MAP kinase to the control to determine the ratio of the phosphorylated MAP kinase to the MAP kinase (cf. Table 5). In Table 5, "MAPK" means a MAP kinase and "pMAPK" means a phosphorylated MAP kinase. "10", "30", "100" and "300" in Table 5 show the examples where 10 μg/ml, 30 μg/ml, 100 μg/ml and 300 μg/ml of the compound 1 were added.

TABLE 5

|  | pMAPK/MAPK | pMAPK/MAPK/Control |
| --- | --- | --- |
| Control | 487 | — |
| 300 | 2234 | 4.59 |
| 100 | 1043 | 2.14 |
| 30 | 1071 | 2.20 |
| 10 | 674 | 1.38 |

Table 5 shows that, as compared with the control, the compound 1 has a high activation (phosphorylation) of MAP kinase. Particularly in the administering example of 300 μg/ml, the activity of around four-fold of the control is shown and it was suggested that the compound 1 has the neurotrophic factor-like activity.

Test Example 2

Evaluation of Activation (Phosphorylation) of MAP Kinase

MAP kinase and phosphorylated MAP kinase were measured for the compound 6 ((E)-2-(diethylamino)ethyl dec-2-enoate) and the compound 13 ((E)-2-(2-(diethylamino)ethoxy)ethyl dec-2-enoate) by the same method as in Test Example 1.

Each of the compounds 6 and 13 was dissolved in 0.1% DMSO to adjust to the concentration of 250 μg/ml. With regard to the control, 0.1% DMSO was added. With regard to the concentration of the resulting band of the gel subjected to electrophoresis, its intensity was calculated by the same method as in Test Example 1 using Image J (K. K. Bioarts) and the ratio of the phosphorylated MAP kinase to the control was divided by the resulting ratio of the MAP kinase to the control whereupon the ratio of the phosphorylated MAP kinase to the MAP kinase was determined (cf. Table 6).

TABLE 6

|  | pMAPK/MAPK/Control |
| --- | --- |
| Control | 1.00 |
| Compound 6 | 1.72 |
| Compound 13 | 1.46 |

Table 6 shows that the compounds 6 and 13 have higher activation (phosphorylation) of MAP kinase than the control suggesting that they have a neurotrophic factor-like activity.

Test Example 3

Evaluation of Suppressive Effect for Depressive Symptom as a Result of Stress Loading Male ddY strain mice of seven weeks age were loaded, as the stress, with forced swimming of 6 minutes every day for 2 weeks and the evaluation of suppressive effect for depression symptom was conducted.

Thus, as from the initiation of loading the stress, the compound 1 dissolved in 0.1% DMSO was intraperitoneally administered every day in a dose of 100 μg/kg body weight and the immobility time of the mice upon the forced swimming was measured (n=5). As a control, a phosphate-buffered physiological saline (PBS) was intraperitoneally administered to the mice during two weeks and the immobility time was measured (n=4).

The cases to which no stress was loaded were also administered with each of the compound 1 and the phosphate buffered saline (PBS) as same as in the cases to which the stress was loaded. The immobility time on the thirteenth day from the stress was loaded was measured and the result is shown in FIG. 1. Incidentally the test of significance was conducted by means of a two-way ANOVA, Bonferroni test.

As will be apparent from FIG. 1, the compound 1 significantly shortened the immobility time and suppressed the depression as compared with the control upon being loaded with the stress.

Test Example 4

Evaluation of Repairing Action for the Spinal Cord Injury

Spinal cord injury model rats were prepared and the repairing action of the compound 1 for the spinal cord injury was investigated. The compound 1 was dissolved in a phosphate buffered saline (PBS) and intraperitoneally administered to each spinal cord injury model rat once daily in a dose of 100 μg/kg body weight. As a control, PBS was similarly administered.

(1) Preparation of Spinal Cord Injury Model Rats

Female Wistar rats of seven weeks age were anesthetized with pentobarbital (40 mg/kg), the spinal column was exposed, vertebral arch of the ninth thoracic vertebra was excised and the tenth thoracic cord (T10) was completely cut using a sharp knife. After the back muscle and the skin were satured, paralysis of hind limbs was confirmed to prepare spinal cord injury model rats.

(2) Improvement in Motor Function

Figure 2:
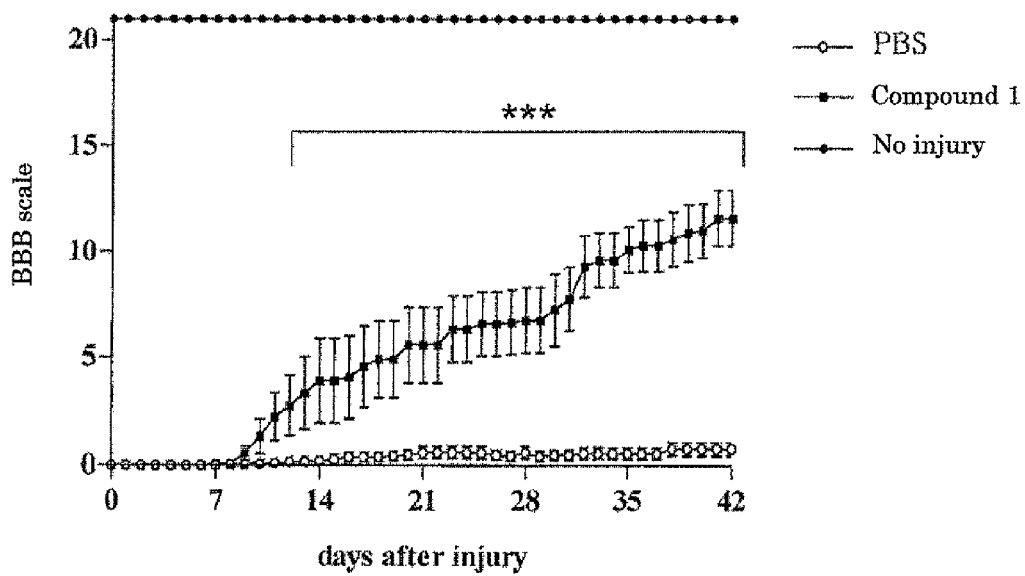
FIG. 2 is a graph showing the improvement in motility function in terms of a BBB scale in spinally injured model rats during six weeks in the groups administered with the compound 1 or the phosphate buffered saline (PBS) in Test Example 4.

For each of the groups administered with the compound 1 and PBS, the improvement in motor function of the spinal cord injury model rats during six weeks was evaluated every day according to a BBB scale (Basso D M, et al., J. Neurotrauma, 12:1-21 (1995)) (0 for immediately after the injury while 21 for non-injury). The result is shown in FIG. 2. Incidentally, the test of significance was conducted by a two-way ANOV, Bonferroni test.

After six weeks, the group administered with the compound 1 recovered to such an extent that, upon resting, the body weight was supported by limb soles whereby the coordinated walking of right and left legs was possible (mean value of BBB scores±SE=11.60±2.2 (n=6)). Further, in the group administered with the compound 1, there were observed some rats which stood up with hind limbs. As shown in FIG. 2, the compound 1 showed a significant difference from the PBS of the control and the improvement in the motor function was significant.

Test Example 5

Evaluation Using PC12 Cells; Immunostaining Method

PC12 cells were stimulated using the compound of the present invention and the phosphorylation of MAPK was evaluated by means of immunostaining of the cells. The specific operation procedure is as follows.

A cover glass was placed on a 24-well plate followed by coating with poly-L-lysine. PC12 cells were seeded in a cell density of 50,000 cells/well. (The amount of the medium was 400 μL) On the first day after seeding the cells, the medium was exchanged to DMEM containing 1% fetal bovine serum (FBS) and 0.06% L-glutamine.

The compound which was previously diluted with DMSO was dissolved in 100 μl of medium. After 12 to 16 hours from the medium exchange, 100 μl out of 400 μl of the medium was removed from each well and, in place of that, 100 μl of a medium containing the compound was added.

After 30 minutes from the addition, fixation was conducted using 4% paraformaldehyde (PFA) for 10 minutes. The fixed cells were washed with a Tris-buffered saline (TBS) and a TBS containing 0.3% Triton X was added thereto followed by incubating at 37° C. for 30 minutes. This was washed with a TBS and blocked with a TBS containing 3% skim milk for 30 minutes (at room temperature).

This was washed with a TBS for one time and a primary antibody (anti-phospho-p42/44 MAPK antibody; cell signalings; #9102 being diluted with TBS to an extent of 1,000-fold) was added thereto followed by subjecting to the reaction at 4° C. for one night. The primary antibody was removed and washed with a TBS for three times. After that, the secondary antibody (Alexa 488 goat anti-rabbit antibody; Invitrogen: being diluted to an extent of 1,000-fold using a TBS containing 1% Block Ace) was added thereto and the reaction was conducted at room temperature for 3 hours. The secondary antibody was removed and, after washing with a TBS, fixation was conducted with 4% PFA for 1 hour.

This was washed with a TBS, Hoechst (diluted with a TBS to an extent of 2000-fold) was added thereto and nuclear staining was conducted. This was washed and mounted.

Taking the photographic pictures and counting the positive cells were conducted as follows. An all-in-one microscope (manufactured by Keyence) was used, exposing time for pMAPK (green) was made 1/2.8 s, the place was appropriately decided in a Hoechst-stained image and the pictures were taken. Four pictures per one glass sheet were taken.

Photoshop (Adobe) was used and the cells having above a certain luminance were judged to be positive. All cells were labeled using Hoechst 33342 manufactured by Invitrogen and the rate of pMAPK-positive cells in Hoechst-positive cells was calculated. (cf. Table 7)

TABLE 7

| | Rate of pMAPK-positive cells (%) | | | | |
|---|---|---|---|---|---|
| | 0 μg/mL | 62.5 μg/mL | 125 μg/mL | 250 μg/mL | 500 μg/mL |
| Compound 1 | 2 | 4 | 12 | 36 | 32 |
| Compound 2 | 0 | 0 | 19 | 71 | 53 |
| Compound 3 | 0 | 0 | 12 | 14 | 14 |
| Compound 4 | 8 | 12 | 27 | 64 | 81 |
| Compound 5 | 4 | 1 | 23 | 0 | 24 |
| Compound 6 | 2 | 31 | 51 | — | — |
| Compound 12 | 1 | 11 | 17 | 9 | 29 |
| Compound 13 | 1 | 35 | 35 | 52 | — |
| Compound 31 | 13 | 79 | 95 | 98 | 96 |
| Compound 36 | 1 | 12 | 70 | 89 | 43 |
| Compound 37 | 1 | 6 | 43 | 48 | 0 |
| Compound 42 | 5 | 6 | 7 | 27 | — |
| Compound 43 | 4 | 20 | 26 | 49 | — |
| Compound 44 | 1 | 17 | 7 | 18 | — |
| Compound 45 | 13 | 34 | 67 | 50 | — |
| Compound 46 | 4 | 22 | 13 | 32 | — |
| Compound 47 | 14 | 17 | 33 | 23 | — |
| Compound 55 | 2 | 20 | 46 | 41 | 10 |

It has been confirmed from Table 7 that, in the evaluation using PC12 cells, the compound of the present invention has a promoting action for MAPK phosphorylation (a neurotrophic factor-like activity).

Test Example 6

Evaluation of Activation (Phosphorylation) of MAP Kinase

With regard to the compound of the present invention, its activation for MAP kinase was measured by the same manner as in Test Example 1.

Each compound was dissolved in 0.1% DMSO to adjust to the concentrations of 30 μg/ml, 60 μg/ml, 125 μg/ml and 250 μg/ml. As to the control, 0.1% DMSO was added.

Intensity of the concentration of the above-obtained band of the gel subjected to electrophoresis was calculated and quantified using Image J (K. K. Bioarts). The numerical value for the MAP kinase using the test compound was divided by the numerical value for the MAP kinase of the control and, further, the numerical value for the phosphorylated MAP kinase using the test compound was divided by the numerical value for the phosphorylated MAP kinase of the control whereupon the ratio of the MAP kinase using the test compound to the control and the ratio of the phosphorylated kinase using the test compound to the control were determined.

After that, the resulting ratio of the phosphorylated kinase to the control was divided by the resulting ratio of the MAP kinase to the control to determine the ratio of the phosphorylated MAP kinase to the MAP kinase (cf. Table 8).

TABLE 8

|  | Ratio of pMAPK to MAPK | | | | |
| --- | --- | --- | --- | --- | --- |
|  | 0 µg/mL | 30 µg/mL | 60 µg/mL | 125 µg/mL | 250 µg/mL |
| Compound 4 | 1.0 | 2.2 | 3.2 | 20.6 | — |
| Compound 13 | 1.0 | 2.6 | 3.1 | 1.3 | — |
| Compound 36 | 1.0 | 1.6 | 5.1 | 0.5 | — |
| Compound 37 | 1.0 | — | 3.4 | 3.4 | 4.9 |
| Compound 55 | 1.0 | 4.6 | 8.6 | 16.0 | — |
| Compound 56 | 1.0 | — | 5.0 | 7.4 | 5.7 |

It was suggested from Table 8 that the compound of the present invention shows higher activation of MAP kinase (phosphorylation) as compared with the control and that an excellent neurotrophic factor-like activity is available.

Incidentally, in Test Examples 1, 2 and 6, nerve cells cultured from the cerebral cortex were used and, in Test Example 5, PC12 cells which are the established cells derived from chromaffin cells of adrenal medulla were used whereby it is able to be concluded that Test Example 6 is the result of the evaluation under the condition which is nearer that in viva Test Example 7

Evaluation of Suppressive Effect for Depressive Symptom as a Result of Loading the Mild Stress Female ddY strain mice of seven weeks age (n=8 to 12) were (A) subjected to forced swimming for 15 minutes and then to normal breeding for two clays, (B) subjected to breeding in an inclined cage for two days and then to normal breeding for one day, (C) subjected to breeding for one day where the floor mat was made wet and then to normal breeding for one day and (D) subjected to breeding for one day using a cage which was rotated at the rate of 180 rotations/minute and then to normal breeding for one clay. Further, (B) to (D) were repeated for two times and stress was loaded for three weeks in total to prepare chronic mild stress-induced depression model mice. During that time, the compound of the present invention dissolved in PBS or in a PBS solvent containing DMSO, etc. was orally administered once daily for three weeks and, after that, the suppressive effect for depressive symptom was evaluated by means of a tail suspension test. Thus, the area which was 1 cm from the tip of the tail of a mouse was grasped with hand and kept at the height of 10 cm from the floor, an observation was conducted for six minutes and the length of immobility time which is an index for the depressive symptom was measured. Incidentally, the test of significance was carried out by a one-way ANOVA, Tukey's Multiple Comparison Test.

As a result of the above tail suspension test, the immobility time for the control group (to which PBS was orally administered) was 103.18±15.96 seconds while the immobility time for the group administered with the compound 55 of the present invention in a dose of 1,500 µg/kg was 63.72±10.13 seconds whereby a significant suppressive effect for depressive symptom was noted. Further, the immobility time for the group administered with the compound 6 of the present invention in a dose of 1,500 mg/kg was 80.67±23.94 seconds whereby suppression for the depressive symptom was noted.

Test Example 8

Evaluation of Suppressive Effect for Anxiety Symptom as a Result of Loading the Mild Stress The same operation as in the above Test Example 7 was conducted to prepare chronic mild stress-induced depressive model mice (n=8 to 12). During that time, the compound of the present invention dissolved in PBS or in a PBS solvent containing DMSO, etc. was orally administered once daily for three weeks and, after that, the suppressive effect for anxiety symptom was evaluated by means of an elevated plus maze test. Thus, time when the mouse stayed in an open arm of the elevated plus maze and the frequency (motility amount) of coming in and out of the mouse for both open arm and closed arm were measured. When the anxiety symptom was stronger, the staying time in the open arm was shorter. At that time, it is confirmed that there is no difference in the frequencies for coming in and out the arm between the cases where the stress is and is not loaded. Incidentally, the test for significance was carried out by a one-way ANOVA, Tukey's Multiple Comparison Test.

As the result of the above elevated plus maze test, the staying time of the control group in an open arm was 25.37±4.13 seconds while the staying time, in an open arm, of the group administered with the compound 6 of the present invention in a dose of 1,500 µg/kg was 53.57±7.00 seconds whereby a significant suppressive effect for anxiety symptom was noted. Further, the staying time, in an open arm, of the group administered with the compound 55 of the present invention in a dose of 1,500 µg/kg was 47.24±7.52 seconds whereby a suppressive effect for anxiety symptom was noted.

Test Example 9

Evaluation of Learning and Memorizing Behaviors of Chronic Mild-Stress Depressive Model Mice The same operation as in the above Test Example 7 was conducted to prepare chronic mild stress-induced depressive model mice (n=8 to 12). During that time, the compound of the present invention dissolved in PBS or in a PBS solvent containing DMSO, etc. was orally administered once daily for three weeks and, after that, evaluation for learning and memorizing behaviors was conducted by means of a spontaneous alternation behavior test (Y-maze test). Thus, an animal was placed at the front end of any arm in the Y-maze and allowed to freely walk in the maze for ten minutes, the arms into which the animal entered were successively recorded and the entry numbers of the animal into each arm within a measuring time (total arm entries) and the combined entry numbers into continuously different three arms (alternating behavior numbers) were checked. The alternating behavior rate (%) was calculated by the following expression and the spontaneous alternating behavior was evaluated as an index of short-term memory. Incidentally, the test of significance was conducted by a one-way ANOVA, Tukey's Multiple Comparison Test.

Alternating behavior rate (%)=(Alternating behavior numbers)/(Total arm entries−2)×100

As a result of the above spontaneous alternating behavior test, the alternating behavior rates of the group administered with the compound of the present invention were 75.40±3.22% for the group administered with the compound 6 of the present invention (300 µg/kg) (the alternating behavior rate of the control group: 60.21±2.39%) and 71.52±2.50% for the group administered with the compound 36 of the present invention (1,500 μg/kg) (the alternating behavior rate of the control group: 61.76±2.01%) whereupon a significant improving effect for a short-term memory function was noted.

It has been suggested in recent years that, when secretion of adrenocortical hormone continues caused by chronic stress or depression, hippocampal cells participating in memory in the brain were killed and dementia is induced from a memory disorder. It has been shown in the above-mentioned activation test for MAP kinase that the compound of the present invention has a neurotrophic factor-like action and is useful for a neurodegenerative disease such as dementia or Alzheimer's disease. It has now been also suggested according to the present test using animals that the compound of the present invention has an improving action for learning and memorizing abilities.

Test Example 10

Evaluation of Suppressive Effect for Depressive Symptom by Administration of Corticosterone Corticosterone suspended in oil was hypodermically injected to male mice of seven weeks age (n=3 to 5) in a dose of 20 μg/kg/day every day for three weeks. At the same time, the compound of the present invention dissolved in PBS or in a PBS solvent containing DMSO, etc. was orally administered every day for three weeks. After one, two and three week(s), the suppressive effect for depressive symptom was evaluated by a tail suspension test in the same manner as in the above Test Example 7. Incidentally, the test for significance was conducted by a Student's t-test.

As a result of the above tail suspension test, the measurement after two weeks showed that the immobility time of the control group was 141.15 seconds while the immobile time of the group administered with the compound of the present invention was 60.37 seconds in the group administered with the compound 6 of the present invention (300 μg/kg), 41.63 seconds in the group administered with the compound 36 of the present invention (300 μg/kg) and 86.71 seconds in the group administered with the compound 55 of the present invention (1,500 μg/kg) whereupon suppression of depressive symptom was noted.

Test Example 11

Evaluation of Repairing Action for Spinal Cord Injury (1) Preparation of Disablement Model Rats with Hemi-Transection of Spinal Cord and Administration of Test Drugs Female Wistar rats of seven weeks age (body weight: 120 to 140 g) were anesthetized with pentobarbital (40 mg/kg), thoracic vertebrae were detached to expose the thoracic cord and the left half thereof was cut at the position of the tenth thoracic cord using a sharp razor. After that, the muscle and the skin were satured to prepare disablement model rats with hemi-transection of spinal cord.

The compound of the present invention was dissolved in PBS or in a PBS solvent containing DMSO, etc. and orally administered once daily for 21 to 31 days.

(2) Evaluation of Improvement in Motor Function

With regard to the group administered with the compound of the present invention (n=3 to 6) and the control group (n=3 to 6), the improvement in motor function of the disablement model rats with hemi-transection of spinal cord was evaluated by a BBB scale (Basso D M, et al., J. Neurotrauma 12:1-21 (1995). Thus, evaluation of motor function was conducted for hind limbs of rats in such respects that whether the joint moves, whether body weight is applied onto the foot, whether walking is done, etc. wherein the movement of the hind limbs was divided into 21 points from no motility to normal state. Incidentally, the test for significance was conducted by a two-way ANOVA, Bonferroni Post test.

As a result of the above improvement test for motor function, BBB scores of the compound of the present invention were 8.3 after nine days in the group administered with the compound 6 of the present invention (100 μg/kg) (BBB score after 9 days in the control group: 3.5), 12.3 after fifteen days in the group administered with the compound 36 of the present invention (500 μg/kg) (BBB score after 15 days in the control group: 9.8) and 5.3 and 12.3 after seven days and fourteen days, respectively, in the group administered with the compound 55 of the present invention (500 μg/kg) (BBB scores after 7 days and 14 days in the control group were 1.8 and 8.5, respectively) whereupon the significant improving effect for motor function was noted.

Test Example 12

Evaluation for Rat Peripheral Nerve Disorder Induced by Paclitaxel

The effect of the compound of the present invention was tested for a peripheral nerve disorder which is a side effect induced by the administration of paclitaxel (an anti-cancer agent) such as hyperesthesia including allodynia (severe pain induced by such tactile stimuli which usually cause no pain). The compound of the present invention was intraperitoneally administered to rats as a test drug to conduct a von Frey test.

(1) Preparation of Paclitaxel-Induced Peripheral Nerve Disorder Rats and Administration of Test Drugs Male SD rats of six weeks age (one group comprising six rats) were used as experimental animals and paclitaxel (2 mg/kg) was intraperitoneally administered every other day for four times in total to prepare paclitaxel-induced peripheral nerve disorder rats. During 18 and 25 days or during 20 to 27 days after initiation of paclitaxel administration, the test drug was intraperitoneally administered in a single dose of 300 μ/kg and the following von Frey test was conducted.

(2) von Frey Test

The rats of the above (1) were placed in a transparent acrylic cage with a wire-meshed floor and habituated for about three minutes and the 50% reaction threshold values to the mechanical stimulus of right hind limb were measured before administration of the test drug and after 1, 5 and 24 hours from initiation of the administration.

The measurement was conducted using von Frey filaments (manufactured by North Coast Medical Inc.) in accordance with the methods of Chaplan, et al. (Journal of Neuroscience Methods, vol. 53, no. 1, pages 55 to 63, 1994) and Dixon, et al. (Annual Review of Pharmacology and Toxicology, vol. 20, pages 441 to 462, 1980). In eight filaments [stimulus loads (g): 0.4, 0.6, 1.0, 2.0, 4.0, 6.0, 8.0 and 15.0], the test was started as from the filament of 2.0 g, the filament was vertically attached to the sole for 2 to 3 seconds with such a force that the filament was lightly bent and the case where the hind limb showed an escape reaction was called a positive reaction. The case where the rat escaped at the instance of removing the filament was also called positive. When the positive reaction was noted, stimulus was conducted similarly using a filament of one rank weaker while, when no reaction was noted, stimulus was conducted similarly using a filament of one rank stronger and the point when the reaction changed from negative to positive or from positive to negative was called the first two reactions. After that, stimulus was conducted for continuous four times by the same up-down method. A 50% reaction threshold value to the mechanical stimulus was measured using the reaction to the six stimuli in total and then (mean value)±(standard error) for each group was calculated. Incidentally, when stimulus reached by that of 15.0 g without positive reaction or, when positive reaction continued to 0.4 g, then 15.0 g or 0.25 g was adopted as each threshold value, respectively. With regard to the higher 50% reaction threshold value between the 50% threshold values after 1 hour and 5 hours from administration of a test drug, a recovery rate (%) of the 50% reaction threshold value was calculated by the following expression in which 15 was adopted as the normal threshold value. An example of the above test results is shown in Table 9.

Recovery rate (%) of 50% reaction threshold value=
[(50% reaction threshold value after 1 hour or 5 hours from administration of test drug)−(50% reaction threshold value before administration of test drug)]/[(Normal threshold value)−(50% reaction threshold value before administration of test drug)]

TABLE 9

| Test drug | Recovery rate of 50% reaction threshold value (%) |
|---|---|
| Compound 1 | 48.3 |
| Compound 2 | 58.1 |
| Compound 8 | 32.2 |
| Compound 9 | 51.4 |
| Compound 10 | 26.4 |
| Compound 11 | 37.6 |
| Compound 15 | 37.7 |
| Compound 16 | 59.7 |
| Compound 17 | 52.6 |
| Compound 18 | 54.6 |
| Compound 19 | 73.7 |
| Compound 20 | 42.5 |
| Compound 21 | 63.2 |
| Compound 22 | 64.6 |
| Compound 23 | 28.6 |
| Compound 24 | 56.1 |
| Compound 25 | 33.7 |
| Compound 26 | 55.7 |
| Compound 27 | 46.4 |
| Compound 28 | 19.4 |
| Compound 29 | 46.3 |
| Compound 31 | 43.1 |
| Compound 32 | 70.6 |
| Compound 33 | 45.3 |
| Compound 34 | 48.3 |
| Compound 35 | 47.1 |
| Compound 36 | 72.1 |
| Compound 37 | 73.1 |
| Compound 38 | 52.1 |
| Compound 39 | 49.7 |
| Compound 40 | 71.5 |
| Compound 41 | 28.3 |
| Compound 42 | 48.7 |
| Compound 43 | 40.3 |
| Compound 44 | 62.6 |
| Compound 45 | 37.0 |
| Compound 46 | 19.9 |
| Compound 47 | 37.4 |
| Compound 48 | 50.7 |
| Compound 49 | 69.3 |
| Compound 50 | 51.7 |
| Compound 51 | 45.7 |
| Compound 52 | 18.7 |
| Compound 53 | 34.9 |
| Compound 54 | 51.9 |
| Compound 55 | 45.4 |
| Compound 56 | 60.5 |

Table 9 shows that the compound of the present invention exhibits an excellent improving effect for hyperesthesia induced by administration of paclitaxel and thus has an alleviating action for the side effect induced by administration of anti-cancer agents. Further, the compound of the present invention also shows an excellent improving action to hyperesthesia when oxaliplatin of platinum drugs is used in the same manner as in the use of paclitaxel of taxane drugs.

INDUSTRIAL APPLICABILITY

As will be apparent from the result of the above pharmacological tests, the compound of the present invention showed an excellent MAP kinase phosphorylating action (neurotrophic factor-like activity) in the evaluation using the nerve cells cultured from the cerebral cortex of rats or PC12 cells. Further, in the animal experiments, administration of the compound of the present invention also showed the action which suppresses the depressive symptom and the result which improves the learning/memorizing ability in various tests using stress-loaded mice. Still further, in the motor function test using spinal cord injury model rats, significant improvement in motor function was shown and a repairing action for injury of spinal cord was confirmed. Accordingly, the compound of the present invention is expected as a preventive or treating agent for dementia, Alzheimer's disease, Parkinson's disease, depression, etc. and as a repairing agent for spinal cord injury and is useful as a pharmaceutical agent.

Furthermore, the compound of the present invention is recognized to have an excellent treating effect for a peripheral nerve disorder in the test conducted using the peripheral nerve disorder being a side effect induced by administration of paclitaxel which is an anti-cancer agent or, in other words, the hyperesthesia caused by mechanical stimulus as an index for a peripheral nerve disorder. Accordingly, the compound of the present invention is effective as a pharmaceutical agent for alleviating the side effect such as a neurological disorder of peripheral nerve system induced by anti-cancer agents including paresthesia such as numbness in terminals of four limbs of humans and animals and hyperalgesia such as pain whereby it has a quite high usefulness.

The invention claimed is:

1. A trans-2-decenoic acid derivative represented by the following formula (1') or a pharmaceutically acceptable salt thereof;

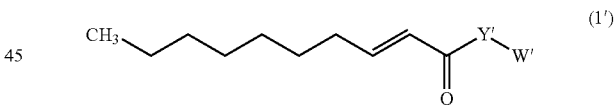

wherein Y' is —O—, —NR'— or —S—;
W' is W1' when Y' is —O—, W2' when Y' is —NR'— or W3' when Y' is —S—; R' is dialkylaminoalkyl group, alkyl group, or hydrogen atom:
(1) W1' is dialkylaminoalkyl group, alkylthioalkyl group, alkoxyalkyl group, dialkoxyalkyl group or dialkylaminoalkoxyalkyl group;
(2-1) W2' is hydrogen atom, alkyl group or dialkylaminoalkyl group when R' is dialkylaminoalkyl group;
(2-2) W2' is alkyl group which is same as or different from R' when R' is alkyl group (except the case where both R' and W2' are ethyl group or methyl group); or
(2-3) W2' is alkyl group (except 2-methylpropyl group and 2-methylbutyl group), cyclohexyl group or pyrrolidinealkyl group when R' is hydrogen atom; and
(3) W3' is alkyl group, cycloalkyl group, phenylalkyl group or dialkylaminoalkyl group.

2. The trans-2-decenoic acid derivative or a pharmaceutically acceptable salt thereof according to claim 1, wherein Y' is —O— and W1' is dialkylaminoalkyl group, alkylthioalkyl group, alkoxyalkyl group, dialkoxyalkyl group or dialkylaminoalkoxyalkyl group.

3. The trans-2-decenoic acid derivative or a pharmaceutically acceptable salt thereof according to claim 1, wherein Y' is —NR'—.

4. The trans-2-decenoic acid derivative or a pharmaceutically acceptable salt thereof according to claim 3, wherein R' is dialkylaminoalkyl group and W2' is hydrogen atom, alkyl group or dialkylaminoalkyl group.

5. The trans-2-decenoic acid derivative or a pharmaceutically acceptable salt thereof according to claim 3, wherein R' is alkyl group and W2' is alkyl group which is same as or different from R' (except the case where both R' and W2' are ethyl group or methyl croup).

6. The trans-2-decenoic acid derivative or a pharmaceutically acceptable salt thereof according to claim 3, wherein R' is hydrogen atom and W2' is alkyl group (except 2-methylpropyl group and 2-methylbutyl group), cyclohexyl group or pyrrolidinealkyl group.

7. The trans-2-decenoic acid derivative or a pharmaceutically acceptable salt thereof according to claim 1, wherein Y' is —S— and W3' is alkyl group, cycloalkyl group, phenylalkyl group or dialkylaminoalkyl group.

8. A pharmaceutical composition comprising a trans-2-decenoic acid derivative according to claim 1.

9. The pharmaceutical composition according to claim 8, wherein Y' is —O— and W1' is dialkylaminoalkyl group, alkylthioalkyl group, alkoxyalkyl group, dialkoxyalkyl group or dialkylaminoalkoxyalkyl group.

10. The pharmaceutical composition according to claim 8, wherein Y' is NR'—.

11. The pharmaceutical composition according to claim 10, wherein R' is dialkylaminoalkyl group and W2' is hydrogen atom, alkyl group or dialkylaminoalkyl group.

12. The pharmaceutical composition according to claim 10, wherein W is alkyl group and W2' is alkyl group which is same as or different from R' (except the case where both R' and W2' are ethyl group and methyl group).

13. The pharmaceutical composition according to claim 10, wherein R' is hydrogen atom and W2' is alkyl group (except 2-methylpropyl group and 2-methylbutyl group), cyclohexyl group, or pyrrolidinealkyl group.

14. The pharmaceutical composition according to claim 8, wherein Y' is —S— and W3' is alkyl group, cycloalkyl group, phenylalkyl group or dialkylaminoalkyl group.

15. The pharmaceutical composition according to claim 8, where the pharmaceutical composition is in a form suitable for preventing or treating a nervous disorder.

16. The pharmaceutical composition according to claim 15, wherein the nervous disorder is a neurodegenerative disease.

17. The pharmaceutical composition according to claim 16, wherein the neurodegenerative disease is dementia, Alzheimer's disease, Parkinson's disease, amyotrophic lateral sclerosis (ALS), Huntington's disease, progressive supranuclear palsy (PSP) or diabetic neuropathy.

18. The pharmaceutical composition according to claim 15, wherein the nervous disorder is a mental disease.

19. The pharmaceutical composition according to claim 18, wherein the mental disease is depression.

20. The pharmaceutical composition according to claim 18, wherein the mental disease is anxiety disorder (neurosis).

21. The pharmaceutical composition according to claim 8, where the pharmaceutical composition is in a form suitable for treating or repairing spinal cord injury.

22. The pharmaceutical composition according to claim 8, where the pharmaceutical composition is in a form suitable for alleviating side effect induced by administration of anti-cancer agents.

23. The pharmaceutical composition according to claim 22, wherein the side effect induced by administration of anti-cancer agents is a peripheral nerve disorder.

* * * * *